(12) United States Patent
Smouse et al.

(10) Patent No.: US 9,956,100 B2
(45) Date of Patent: May 1, 2018

(54) SYSTEMS AND METHODS FOR COUPLING AND DECOUPLING A CATHETER

(71) Applicant: BRIGHTWATER MEDICAL, INC., Peoria Heights, IL (US)

(72) Inventors: Harry R. Smouse, Peoria Heights, IL (US); Kent C. B. Stalker, San Marcos, CA (US); Timothy H. Williams, Palo Alto, CA (US); Eugene R. Serina, Fremont, CA (US)

(73) Assignee: BrightWater Medical, Inc., Dunlap, IL (US)

( * ) Notice: Subject to any disclaimer, the term of this patent is extended or adjusted under 35 U.S.C. 154(b) by 85 days.

(21) Appl. No.: 14/823,243

(22) Filed: Aug. 11, 2015

(65) Prior Publication Data

US 2016/0045347 A1 Feb. 18, 2016

Related U.S. Application Data

(60) Provisional application No. 62/036,377, filed on Aug. 12, 2014.

(51) Int. Cl.
*A61F 2/95* (2013.01)
*A61M 27/00* (2006.01)

(52) U.S. Cl.
CPC .............. *A61F 2/95* (2013.01); *A61M 27/008* (2013.01); *A61F 2002/9511* (2013.01); *A61F 2002/9517* (2013.01)

(58) Field of Classification Search
CPC ..................... A61F 2002/48; A61F 2/95; A61F 2002/9511; A61M 27/008
See application file for complete search history.

(56) References Cited

U.S. PATENT DOCUMENTS 818,817 A 4/1906 Leva
4,350,161 A 9/1982 Davis, Jr.
(Continued)

FOREIGN PATENT DOCUMENTS

CN 2128148 Y 3/1993
CN 2408894 Y 12/2000
(Continued)

OTHER PUBLICATIONS

Office action dated Oct. 7, 2015 for U.S. Appl. No. 14/159,221.
(Continued)

*Primary Examiner* — Thomas J Sweet
*Assistant Examiner* — Daniel Bissing
(74) *Attorney, Agent, or Firm* — Wilson, Sonsini, Goodrich & Rosati

(57) ABSTRACT

A convertible nephroureteral catheter is used in the treatment of urinary system complications, particularly on the need for a single surgically delivered device to treat patients who must be seen by an interventional radiologist (IR). In many current procedures, patients need to return to the operating room to remove a previously delivered nephroureteral catheter to exchange this catheter with a fully implanted ureteral stent delivered though the same access site at the flank. The present convertible nephroureteral catheter reduces the need to return for a second surgical procedure. Two weeks after initial implantation, the proximal portion of the convertible nephroureteral catheter extending out from the body may simply be removed. A simple action at the catheter hub allows this proximal portion to be removed, leaving behind the implanted ureteral stent within the patient's urinary system. Other medical procedures, devices, and technologies may benefit from the described convertible catheter.

12 Claims, 27 Drawing Sheets

(56) References Cited

U.S. PATENT DOCUMENTS

| | | | |
|---|---|---|---|
| 4,790,810 A | 12/1988 | Pugh, Jr. et al. | |
| 4,957,479 A | 9/1990 | Roemer | |
| 5,122,136 A | 6/1992 | Guglielmi et al. | |
| 5,507,732 A | 4/1996 | Mcclure et al. | |
| 5,643,254 A | 7/1997 | Scheldrup et al. | |
| 5,876,417 A | 3/1999 | Devonec et al. | |
| 5,921,952 A | 7/1999 | Desmond, III et al. | |
| 5,964,771 A | 10/1999 | Beyar et al. | |
| 6,248,100 B1 | 6/2001 | De et al. | |
| 6,264,624 B1 | 7/2001 | Desmond, III et al. | |
| 6,319,287 B1 | 11/2001 | Frimberger | |
| 6,562,024 B2 | 5/2003 | Toledo et al. | |
| 6,569,150 B2 | 5/2003 | Teague et al. | |
| 6,576,008 B2 | 6/2003 | Devonec et al. | |
| 6,629,981 B2 | 10/2003 | Bui et al. | |
| 6,673,106 B2 | 1/2004 | Mitelberg et al. | |
| 6,676,651 B2 | 1/2004 | Haacke et al. | |
| 6,913,625 B2 | 7/2005 | Segura et al. | |
| 6,929,664 B2 | 8/2005 | Kolb et al. | |
| 6,949,125 B2 | 9/2005 | Robertson | |
| 6,991,614 B2 | 1/2006 | Mcweeney et al. | |
| 7,044,980 B2 | 5/2006 | Hammond et al. | |
| 7,044,981 B2 | 5/2006 | Liu et al. | |
| 7,169,139 B2 | 1/2007 | Teague et al. | |
| 7,217,250 B2 | 5/2007 | Kolb et al. | |
| 7,367,987 B2 | 5/2008 | Balgobin et al. | |
| 7,371,252 B2 | 5/2008 | Balgobin et al. | |
| 7,377,932 B2 | 5/2008 | Mitelberg et al. | |
| 7,550,002 B2 | 6/2009 | Goto et al. | |
| 7,731,676 B2 | 6/2010 | Maeda | |
| 7,811,305 B2 | 10/2010 | Balgobin et al. | |
| 7,824,367 B2* | 11/2010 | Accisano, III | A61M 25/0017 604/541 |
| 7,901,444 B2 | 3/2011 | Slazas | |
| 7,901,704 B2 | 3/2011 | Richard | |
| 7,993,329 B2 | 8/2011 | Howell et al. | |
| 8,007,540 B2 | 8/2011 | Robertson | |
| 8,021,434 B2 | 9/2011 | Segura et al. | |
| 8,034,094 B2 | 10/2011 | Aoba et al. | |
| 8,070,825 B2 | 12/2011 | Devonec | |
| 8,298,276 B2 | 10/2012 | Ozawa et al. | |
| 8,333,000 B2 | 12/2012 | Huang et al. | |
| 8,333,796 B2 | 12/2012 | Tompkins et al. | |
| 8,603,185 B2 | 12/2013 | Shah et al. | |
| 8,657,884 B2 | 2/2014 | Smouse | |
| 8,676,349 B2 | 3/2014 | Stalker et al. | |
| 8,702,784 B2 | 4/2014 | Weisman et al. | |
| 8,753,303 B2 | 6/2014 | Weisman et al. | |
| 8,771,335 B2 | 7/2014 | Griego et al. | |
| 8,961,581 B2 | 2/2015 | Hollett et al. | |
| 8,979,824 B2 | 3/2015 | Amos et al. | |
| 8,986,364 B2 | 3/2015 | Okuma | |
| 9,026,229 B2 | 5/2015 | Stalker et al. | |
| 9,186,151 B2 | 11/2015 | Tompkins et al. | |
| 9,265,637 B2 | 2/2016 | Weisman et al. | |
| 9,308,359 B2 | 4/2016 | Ward | |
| 9,314,359 B2 | 4/2016 | Windheuser et al. | |
| 9,387,312 B2 | 7/2016 | Smouse et al. | |
| 9,510,962 B2 | 12/2016 | Aoba et al. | |
| 9,517,120 B2 | 12/2016 | Devonec et al. | |
| 9,597,207 B2 | 3/2017 | Weisman et al. | |
| 2003/0163204 A1 | 8/2003 | Rix | |
| 2003/0191450 A1 | 10/2003 | Teague et al. | |
| 2003/0195456 A1 | 10/2003 | Robertson | |
| 2004/0073283 A1 | 4/2004 | Ewers | |
| 2004/0181186 A1 | 9/2004 | Gellman et al. | |
| 2004/0249343 A1 | 12/2004 | Cioanta | |
| 2005/0085892 A1 | 4/2005 | Goto et al. | |
| 2007/0078446 A1 | 4/2007 | Lavelle | |
| 2007/0112420 A1 | 5/2007 | Laduca | |
| 2007/0233223 A1 | 10/2007 | Styrc et al. | |
| 2007/0276466 A1 | 11/2007 | Lavelle et al. | |
| 2008/0109059 A1 | 5/2008 | Gordon et al. | |
| 2008/0140101 A1 | 6/2008 | Carley et al. | |
| 2008/0221554 A1 | 9/2008 | O'Connor et al. | |
| 2009/0048654 A1 | 2/2009 | Chmura et al. | |
| 2009/0099640 A1 | 4/2009 | Weng | |
| 2009/0105719 A1 | 4/2009 | Honey et al. | |
| 2009/0248169 A1 | 10/2009 | Li | |
| 2009/0312829 A1 | 12/2009 | Aoba et al. | |
| 2010/0070047 A1 | 3/2010 | Smouse | |
| 2010/0268201 A1* | 10/2010 | Tieu | A61B 17/12022 606/1 |
| 2011/0130821 A1* | 6/2011 | Styrc | A61F 2/95 623/1.11 |
| 2011/0196410 A1* | 8/2011 | Besselink | A61F 2/013 606/191 |
| 2011/0196507 A1 | 8/2011 | St. | |
| 2012/0203325 A1 | 8/2012 | Weisman et al. | |
| 2012/0330397 A1 | 12/2012 | Harrison et al. | |
| 2014/0135941 A1 | 5/2014 | Smouse et al. | |
| 2014/0172065 A1* | 6/2014 | Lavelle | A61M 27/008 623/1.11 |
| 2014/0194970 A1 | 7/2014 | Chobotov | |
| 2014/0200462 A1 | 7/2014 | Stalker et al. | |
| 2014/0309721 A1 | 10/2014 | Griego et al. | |
| 2015/0005864 A1 | 1/2015 | Okuma | |
| 2015/0073525 A1* | 3/2015 | Aoba | A61F 2/82 623/1.11 |
| 2015/0157480 A1 | 6/2015 | Amos et al. | |
| 2015/0223953 A1 | 8/2015 | Pendleton et al. | |
| 2016/0015509 A1 | 1/2016 | McDonough | |
| 2016/0120675 A1 | 5/2016 | Weisman et al. | |
| 2016/0151615 A1 | 6/2016 | Overtoom | |
| 2016/0184123 A1 | 6/2016 | Windheuser et al. | |
| 2016/0287372 A1 | 10/2016 | Smouse et al. | |

FOREIGN PATENT DOCUMENTS

| | | |
|---|---|---|
| CN | 201624817 U | 11/2010 |
| CN | 102548505 A | 7/2012 |
| CN | 102579171 A | 7/2012 |
| CN | 102596083 A | 7/2012 |
| CN | 202537720 U | 11/2012 |
| CN | 202637201 U | 1/2013 |
| CN | 103211671 A | 7/2013 |
| CN | 103876872 A | 6/2014 |
| CN | 103961194 A | 8/2014 |
| WO | WO 1988/005317 A1 | 7/1988 |
| WO | WO-2015108609 A1 | 7/2015 |
| WO | WO-2016025434 A1 | 2/2016 |
| WO | WO-2016042150 A1 | 3/2016 |

OTHER PUBLICATIONS

Notice of allowance dated Oct. 9, 2013 for U.S. Appl. No. 12/559,946.
Office action dated Jan. 3, 2012 for U.S. Appl. No. 12/559,946.
Office action dated Oct. 24, 2012 for U.S. Appl. No. 12/559,946.
Notice of allowance dated May 13, 2016 for U.S. Appl. No. 14/159,221.
International search report and written opinion dated Mar. 25, 2015 for PCT Application No. PCT/US2014/063758.
International search report and written opinion dated 01/07/016 for PCT Application No. PCT/US15/44580.
Office action dated Feb. 26, 2016 for U.S. Appl. No. 14/159,221.
European Search Report and Search Opinion dated Sep. 7, 2017 for European Patent Application No. 14878890.4.
European search report and search opinion dated Dec. 22, 2017 for EP Application No. 15831895.6.

* cited by examiner

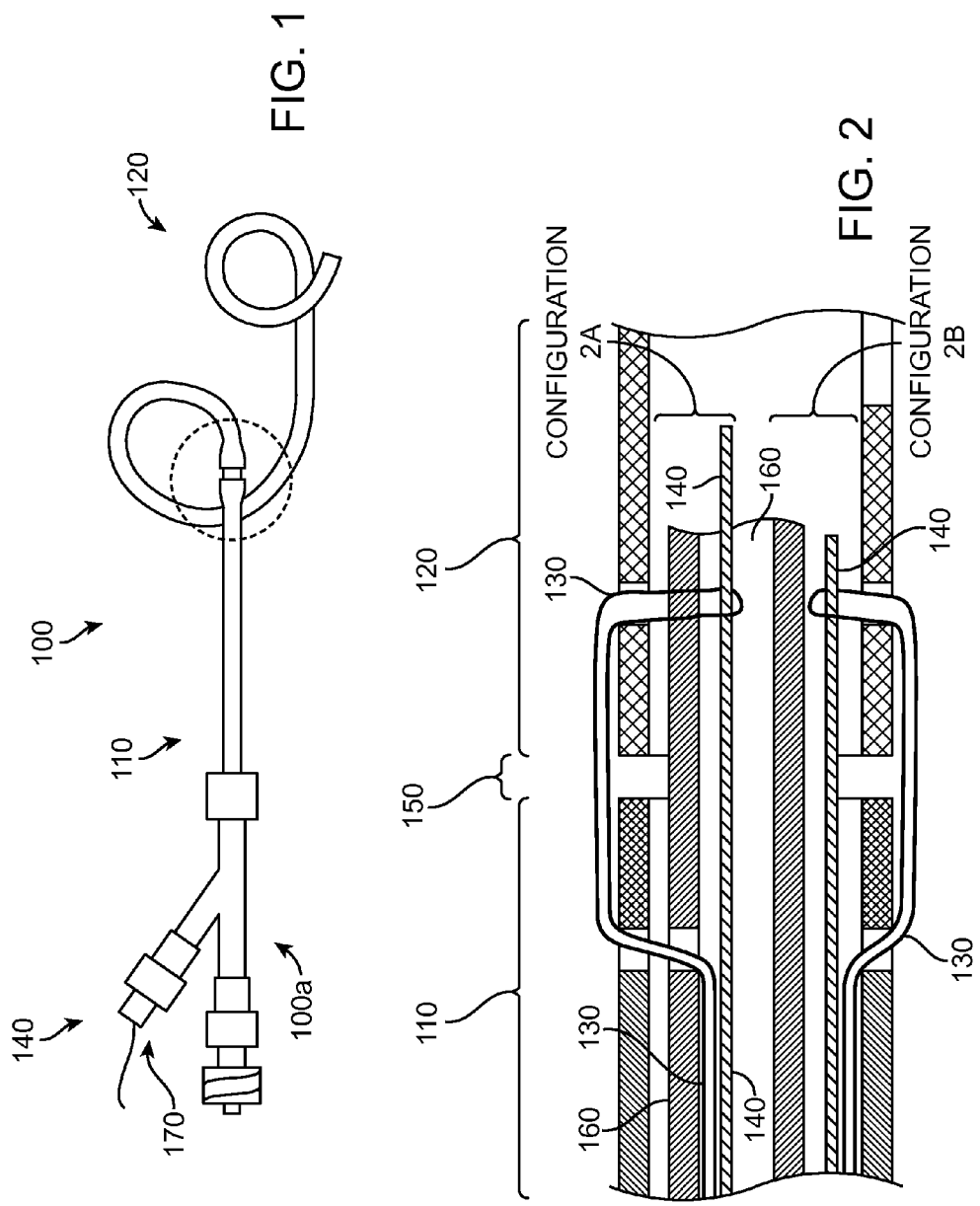

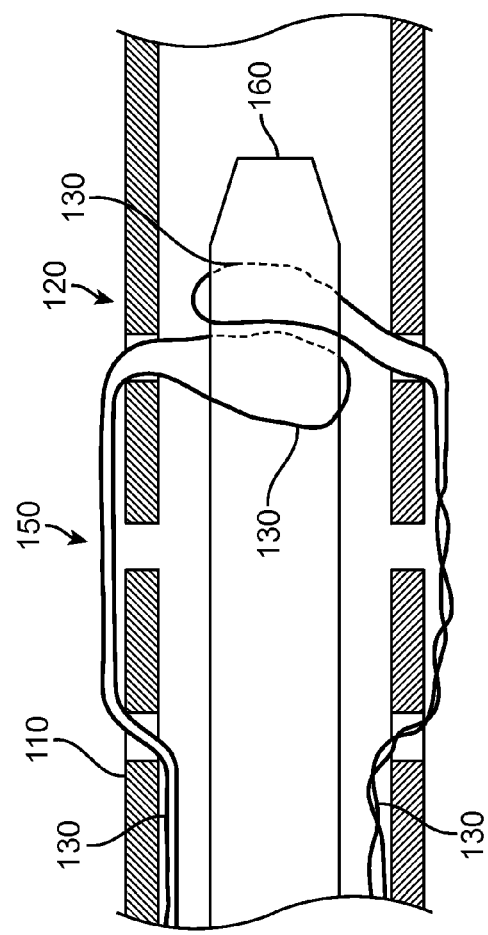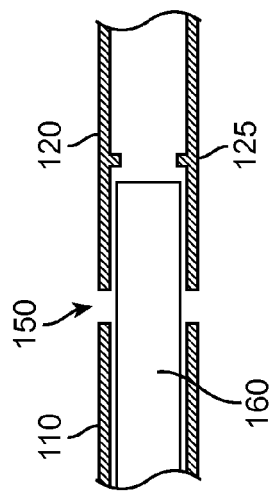

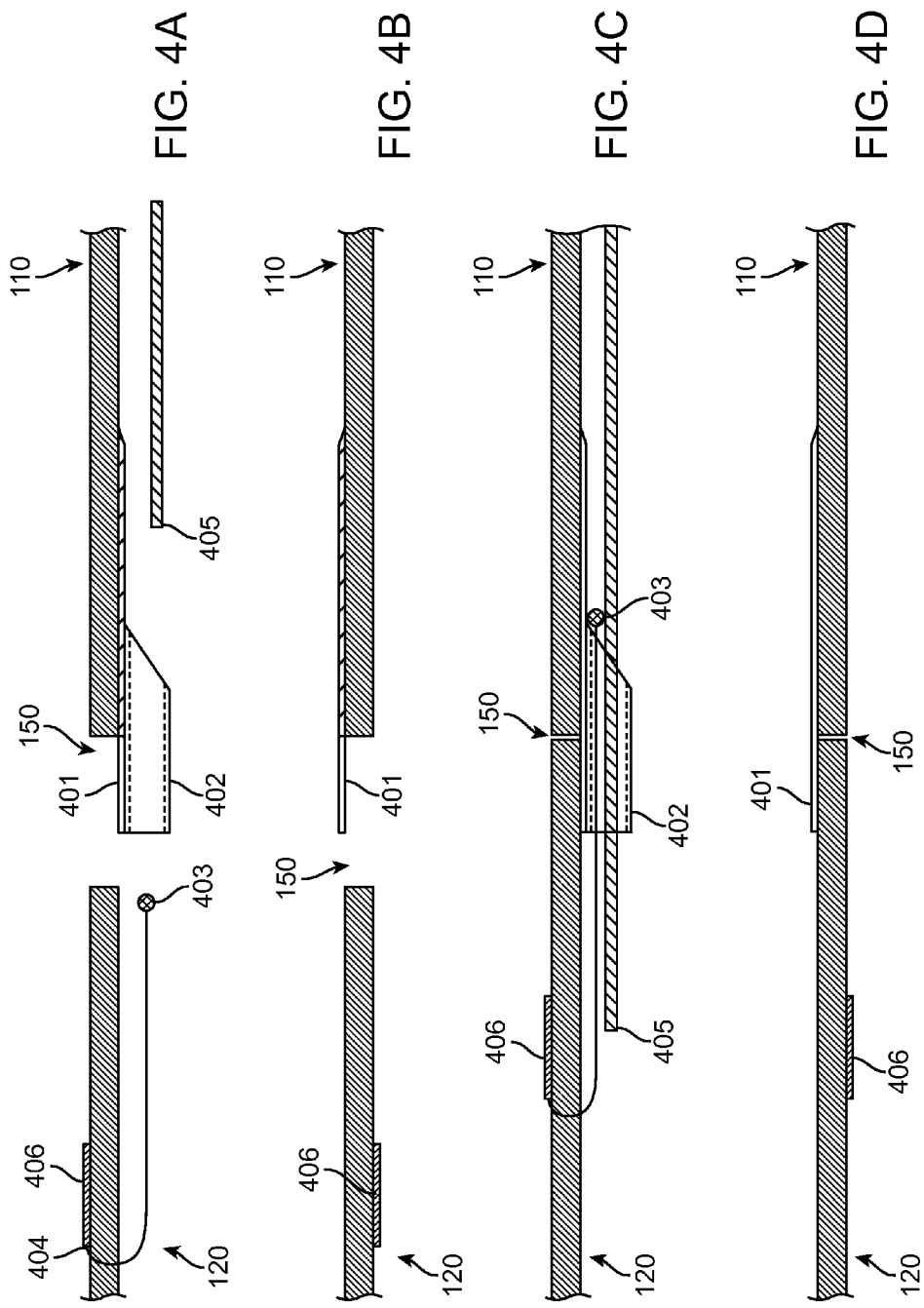

SYSTEMS AND METHODS FOR COUPLING AND DECOUPLING A CATHETER

CROSS-REFERENCE

This application claims the benefit of U.S. Provisional Application No. 62/036,377, filed Aug. 12, 2014, which application is incorporated herein by reference.

The subject matter of this application is related to the subject matter of U.S. patent application Ser. No. 12/559,946, filed Sep. 15, 2009 and now issued as U.S. Pat. No. 8,657,884, and Ser. No. 14/159,221, filed Jan. 20, 2014, which applications are incorporated herein by reference.

BACKGROUND

The ureteral stent is a medical device used within a patient population which experience one or more complications associated with the urinary system which includes the kidneys, ureters and bladder. A host of complications may affect urinary flow and how these organs handle this function; these complications ranging from decreased urine flow to swelling of the kidneys or bladder, with many of these conditions being adversely impacted by the formation of kidney stones. To alleviate urinary system complications, a device or device(s) are placed either within the bladder, one or both of the kidneys, and/or one or both of the patient's ureters. The devices used in these areas are known as nephrostomy catheters (delivered percutaneously within a kidney collecting system), nephroureteral catheters (delivered percutaneously and extending distally into the bladder), urinary catheters (delivered through the urethra), or ureteral stents (delivered percutaneously or through the urethra).

The focus of the present disclosure will surround the delivery method and use of the nephroureteral catheter and the ureteral stent, which are often used one after the other in percutaneous cases to deal with a patient's urinary system complications. Once a patient has exhibited urinary complications and a ureteral stent implantation is recommended, a urologically delivered stent placement will often be attempted. In some cases, this cannot be achieved by the urologist due to a variety of possible factors, resulting in the patient being sent to the interventional radiologist (IR). The IR may then attempts to deliver a nephroureteral stent percutaneously though the backside of the patient and into the impacted kidney, with said device extending distally into the bladder. The proximal end of the nephroureteral catheter thereby remains outside of the patient for up 2 weeks, giving the access site sufficient time to heal before removal. Once the access site has fully healed the patient is typically sent back to the operating room for a second interventional procedure whereby the nephroureteral stent is removed and a ureteral stent is then delivered. This ureteral stent differs from the nephroureteral stent in that its proximal tip terminates within the kidney's renal pelvis. This ureteral stent has a curl at its distal end which resides in the bladder and a proximal curl which resides in the renal pelvis. This device may reside in the patient for up to 6 months or in some cases longer and may be removed urologically. This two-step approach and the devices used may be less than ideal in many cases. There are needs to overcome at least some of their drawbacks.

SUMMARY

According to many embodiments, integrating the functionalities of two existing devices used for the percutaneous treatment of urinary complications into a single device has been devised, with particular focus on the methods, designs and materials which may be utilized to couple these two devices together in a fashion which allows a decoupling at a later time state. Many embodiments provide a single device which may combine the functionalities of a nephroureteral catheter and ureteral stent, but can maintain the ability to perform the full removal of the proximal (catheter) portion of the device extending out of the patient's body during the early stages of implantation (up to 2 weeks).

The decoupling (release) mechanism can allow the proximal portion of this combination device to be removed without the need for a second interventional procedure. The primary modes of function of this coupling mechanism include, but are not limited to, the following: (1) to maintain connection of proximal (catheter) portion of device to distal (stent) portion of device, and (2) to permit the removal of the proximal portion of device at a later time leaving behind distal portion of device within the patient's urinary collecting system. The decoupling nature of the proximal portion of the device may be achieved by providing an input to the proximal hub of the device which extends out of the patient's body. This input to decouple catheter from stent may be performed by the push of a button, the rotation of a luer, the insertion of a tool, the removal of a wire or a series of similar events all occurring at the proximal hub, or the like. Additionally, independent of the coupling mechanism, a strand of material, typically with a circular cross-section, can be used to assist in the closure of the stent's proximal loop once the device has been delivered into the patient. This is often necessary due to the tighter space the renal pelvis provides for this proximal loop to reside. This strand of material may be called the 'proximal loop suture' and may pass through side holes cut into the stent allowing for proximal loop closure. This 'proximal loop suture' may be fully removed from the device without inhibiting the functionality of the coupling interface between the proximal and distal portions of the device.

Several depictions of the coupling interface between the catheter and stent are shown in the Figures. This coupling interface would permit the utilization of a single surgical procedure as opposed to two, putting the patient at significantly less risk for complications in the operating room environment. The decoupling may be achieved by an input to the proximal hub performed at bedside or by the insertion of a decoupling tool, thereby removing catheter portion of device once deemed necessary. A coupled device may be achieved in many ways as described herein. An example of a coupling may include an expandable inner member which retains the distal member with the proximal member by expanding within the stent lumen to couple and once an input is applied to proximal hub, said expanded element may collapse and decouple the device. Some of the depictions below may provide a safe and effective ways to combine the nephroureteral catheter and the ureteral stent while still providing the utility of separate devices and two surgical procedures.

Aspects of the present disclosure provide surgically delivered medical devices. An exemplary medical device may comprise a proximal portion which extends outside of a patient's surgical access site. The proximal portion of device may be removed at a later date, converting the distal portion of device into an implant. The device may comprise a distal (stent) member and a proximal (catheter) member. The proximal and distal members may be coupled to one another in a concentric fashion via an inner member extending out from the proximal member. The proximal and distal members may be coupled in one of or a combination of many embodiments.

In many embodiments, the device may employ suture loop lock(s) to couple the proximal member to the distal member. The suture loop lock(s) may wrap around one or more pull wire(s) at the inner member to stent interface. Furthermore, suture tail(s) may extend proximally to the hub of device and may be locked into place with tension applied to achieve leveraged coupled interface.

In many embodiments, the device may employ suture loop lock(s) which wrap around the inner member at the stent interface region to achieve coupling of proximal and distal members. Furthermore, suture tail(s) may extend proximally to hub of device and may lock into place with tension applied to achieve leveraged coupled interface.

In many embodiments, the device may comprise an inner member which is fixed at the distal region of proximal catheter. The inner member may contain a smaller tube affixed within its lumen. The smaller tube may be used as a receiver for a ball wire, which may extend from distal member, and a pull wire, which may extend from proximal member. Once the ball wire has passed through the smaller tube, the pull wire may be passed through which may prevent passing of ball until pull wire is removed from device.

In many embodiments, the device may comprise an inner member which is fixed at the distal region of the proximal catheter. The inner member may include a superelastic/shape memory element which may be used as a receiver described above.

In many embodiments, the proximal and distal members of the device may be coupled to one another using a ring locking style mechanism, with one ring element affixed to distal member and another ring element affixed to proximal member. The ring members may be held coincident using an inner member and a pull wire.

In many embodiments, the device may comprise a keyed locking system, such as mating hexagonal elements, with one hex element affixed to proximal member and another hex element affixed to distal member to achieve coupling. The hex elements may be engaged or disengaged using a counter rotating tool.

In many embodiments, the inner member may extend fully from proximal hub to achieve concentric junction between the distal and proximal members. In addition, the inner member may be fixed or movable at hub and along entire catheter length.

In many embodiments, the inner member may be a component which is affixed to the distal or proximal member and only extends for a fractional portion of the device's length.

In many embodiments, the inner member may be formed as a necking of the distal region of the catheter itself which is then inserted into the lumen of the distal (stent) member.

In many embodiments, the proximal and distal members of the device may be coupled to one another through the employment of an adhesive layer on the inner member region which extends into the distal member.

In many embodiments, the proximal and distal members of the device may be coupled to one another through the employment of an oversized diameter of the inner member resulting in a frictional fit with the stent.

In many embodiments, the proximal and distal members of the device may be coupled to one another through the employment of a metallic or polymeric crimp which may be applied to the outside of the stent which overlaps the inner member extending into its lumen.

In many embodiments, the proximal and distal members of the device may be coupled to one another through the employment of a superelastic/shape memory alloy affixed to the distal member which may interface with protrusions on the outer surface of the inner member. Thereby, the inner member may not be movable until the catheter or peel-away sheath has been removed and shape memory alloy mechanism releases inner member.

In many embodiments, the proximal and distal members of the device may be coupled to one another through the use of a mechanically modified surface of the inner member which, once inserted into distal member, an interfacing region of the distal member may be heated and a polymer may be allowed to flow into the mechanical alterations of inner member. The polymer may furthermore be allowed to cool, forming a permanent mechanical interface between the two elements until the inner member is pulled away from distal member using a light to moderate pull force.

In many embodiments, the proximal and distal members of the device may be coupled to one another through the use of a female to male thread style arrangement at the coupling interface.

In many embodiments, the proximal and distal members of the device may be coupled to one another using electrically releasable metallic element(s), which may couple the proximal and distal members until a tool can be used to electrically disengage said elements.

In many embodiments, the proximal and distal members of the device may be coupled to one another using magnets affixed to proximal and distal members and may be disengaged by pulling proximal member away from distal member or by rotating one or both of magnetic components within said members using a tool or other components incorporated within device.

In many embodiments, the proximal and distal members of the device in their coupled state may be disengaged using a separate tool which may decouple proximal and distal members by an input of rotation, electrical stimulus or ultrasonic vibration.

Aspects of the present disclosure also provide further stent delivery systems. An exemplary stent delivery system may comprise a catheter body, a stent member, an inner member, and a tether. The catheter body may have an inner lumen and a proximal end and a distal end. The stent member may have an inner lumen and a proximal end releasably coupled with the distal end of the catheter body. The inner member assembly may be disposed in the inner lumen of the catheter body and may extend into the inner lumen of the stent member to concentrically align the catheter body and the stent member. The tether may extend through or along the catheter body and into the inner lumen of the stent member to form a loop over at least a portion of the inner member assembly, thereby securing the stent member to the catheter body. Retraction of the inner member from the inner lumen of the stent member may free the inner member assembly from the loop such that the stent member is released from the stent body.

The inner member assembly may comprise a locking pull wire. The locking pull wire may be threadable through the loop of the tether. The inner member assembly may comprise a hypotube. The inner member assembly may be configured to be actuated with one or more pull tabs or rotatable caps at a hub coupled to the proximal end of the catheter body.

The tether may extend through the inner lumen of the catheter body. The tether may extend out of a lateral port of the catheter body near the distal end of the catheter body. The loop formed by the tether may extend into stent member through a lateral port of the stent member to be threaded through by the at least a portion of the inner member assembly within the inner lumen of the stent member. The tether may have a fixed end near the distal end of the catheter body and a free end. The tether may extend proximally toward the free end and the proximal end of the catheter body. The tether may have a first end and a second end. The tether may extend proximally toward both the first and second ends and the proximal end of the catheter body.

The stent member may comprise a proximal loop and a distal loop. One or more of the proximal loop or the distal loop of the stent member may have a straightened configuration and a looped configuration. One or more of the proximal loop or the distal loop may be biased to assume the looped configuration. The stent delivery system may further comprise a loop pull wire extending through the inner lumen of the catheter body and coupled to the proximal loop. Retracting the loop pull wire may pull the proximal loop into the loop configuration or may lower a radius of the proximal loop. The loop pull wire may extends out from a first lateral port of the stent member near the proximal end of the stent member and may extend back into a second lateral port of the stent member near a distal end of the proximal loop. The loop pull wire may be retractable from a pull tab or rotatable cap at a hub coupled to the proximal end of the catheter body.

Other exemplary stent delivery systems may comprise a catheter body, a catheter member, and an inner member assembly. The catheter body may have an inner lumen and a proximal end and a distal end. The catheter member may have an inner lumen and a proximal end which is fixed or releasably coupled with a stent element extending from within the lumen of the proximal end of the stent body. The inner member assembly may be disposed in the inner lumen of the catheter body and may extend into the inner lumen of the stent member to concentrically align the catheter body and the stent member.

In some embodiments, the stent delivery system further comprises a wire extending through or along the entire or a portion of the catheter body and into the inner lumen of the stent body to interface the catheter member, with the stent element thereby securing the stent body to the catheter body. Retraction of the wire from the inner lumen of the catheter member may free the inner member assembly from the stent element such that the catheter member is released from the stent body.

In some embodiments, the stent delivery system may further comprise a wire extending through or along the entire or a portion of the catheter body and into the inner lumen of the stent member, subsequently interfacing with the superelastic assembly in a releasable fashion to secure the stent member to the catheter body. Retraction of the wire from the inner lumen of the stent member may free the superelastic inner member assembly from such that the stent member is released from the stent body.

In some embodiments, the stent delivery system may further comprise a tether extending through or along the catheter body and into the inner lumen of the stent member to form a loop over at least a portion of the inner member assembly, thereby securing the stent member to the catheter body. Retraction of the inner member from the inner lumen of the stent member may free the inner member assembly from the loop such that the stent member is released from the stent body.

In some embodiments, the stent delivery system may further comprise a tether extending through or along the catheter body and into the inner lumen of the stent member to form a loop over at least a portion of the inner member assembly, thereby securing the stent member to the catheter body. Retraction of the inner member from the inner lumen of the stent member may free the inner member assembly from the loop such that the stent member is released from the stent body.

In some embodiments, the stent delivery system may further comprise an adhesive which is applied to the inner lumen of the stent member to affix the inner member assembly to the stent member extending through or along the catheter body and into the inner lumen of the stent member, thereby securing the stent member to the catheter body. Retraction of the inner member at a threshold load may allow a break away from the bonded surface of the stent member such that the inner member is released from the stent body.

In some embodiments, the stent delivery system may further comprise a frictional interference between the inner member and the stent member. The frictional interference may be applied to the inner lumen of the stent member to affix the inner member assembly to the stent member extending through or along the catheter body and into the inner lumen of the stent member, thereby securing the stent member to the catheter body. Retraction of the inner member at a threshold load may allow a breakaway of the frictional interference with the stent member such that the inner member is released from the stent body.

In some embodiments, the stent delivery system may further comprise a metallic crimp or swaged band element. The metallic crimp or swaged band element may be applied over the outside of the stent body toward its distal end to affix the inner member assembly to the stent member extending through or along the catheter body and into the inner lumen of the stent member thereby securing the stent member to the catheter body. Retraction of the inner member at a threshold load may allow a breakaway from the frictional interference resulting from the crimp element such that the inner member is released from the stent body.

In some embodiments, the stent delivery system may further comprise a superelastic mechanism extending from the stent body. The superelastic mechanism may interface with the inner member in a locked state until the catheter body is removed, at which point the superelastic mechanism may release the inner member from its locked state allowing its complete removal.

In some embodiments, the stent delivery system may further comprise a thermoforming process applied to the inner member allowing it to interface with the stent member to affix the inner member assembly to the stent member extending through or along the catheter body and into the inner lumen of the stent member, thereby securing the stent member to the catheter body. Retraction of the inner member at a threshold load may allow a breakaway from the thermoformed surface of the stent member such that the inner member is released from the stent body.

In some embodiments, an inner member and stent member may interface and lock together via threaded surfaces to affix the inner member assembly to the stent member extending through or along the catheter body and into the inner lumen of the stent member, thereby securing the stent member to the catheter body. Rotation of the inner member out from the stent member may enable inner member to be released from the stent body.

The stent delivery systems may further be configured in any number of ways described above and herein.

Aspects of the present disclosure also provide methods for delivering nephroureteral or other stents. A stent delivery system may be advanced through a percutaneous access site so that a distal end of a stent member of the stent delivery system is positioned in a bladder and a proximal end of the stent member is positioned in a renal pelvis. The distal end of the stent member may form a distal loop in the bladder. The proximal end of stent member may be actuated to form a proximal loop in the renal pelvis. The stent member may be decoupled from a catheter body of the stent delivery system. The catheter body of the stent delivery system may be retracted from the percutaneous access site, leaving the stent member in place.

To actuate the proximal end of the stent member to form a proximal loop in the renal pelvis, a loop pull wire extending through the catheter body may be retracted to reduce a radius of the proximal end of the stent member.

To decouple the stent member from the catheter body, a lock pull wire may be retracted from the stent member to free a tether loop extending into the stent member from the catheter body and/or an inner member may be retracted from the stent member. The inner member may be configured to concentrically align the catheter body with the stent member when advanced therethrough.

The member and the catheter body of the stent delivery system may be left in place for at least 3 days before the stent member is decoupled from the catheter body and the catheter body is retracted from the percutaneous access site. In some embodiments, urine is be drained through the catheter body of the stent left in place. In some embodiments, the catheter body of the stent left in place is capped.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings which display various embodiments of the coupling mechanism to be used in the fabrication of the convertible nephroureteral catheter and are described as follows.

FIG. 1 is a side view of an example convertible nephroureteral catheter, according to many embodiments.

FIG. 2 is a side section view detailing two coupling methods utilizing the principle of a suture loop lock in conjunction with a pull wire, according to many embodiments.

FIGS. 3A and 3B are side section views of a suture loop lock similar to that of the previous figures, but where the inner member of the catheter is grabbed by the suture loop(s) as opposed to using a pull wire, according to many embodiments.

FIGS. 4A, 4B, 4C, and 4D are side section views of the coupling region between the catheter (proximal member) and stent (distal member) with elements that have been affixed to both proximal and distal members which may be used for coupling and decoupling of said members (with decoupling means achieved by removing pull wire from assembled elements), according to many embodiments.

FIGS. 23A, 23B, and 23C show perspective views of the hub. FIG. 23A shows the hub being axially collapsed, FIG. 23B shows the hub being partially separated, and FIG. 23C shows the hub being fully separated out so that multiple pull tabs can be used. FIG. 23D shows a side section view of the hub.

DETAILED DESCRIPTION

Figures 5A, 5B:
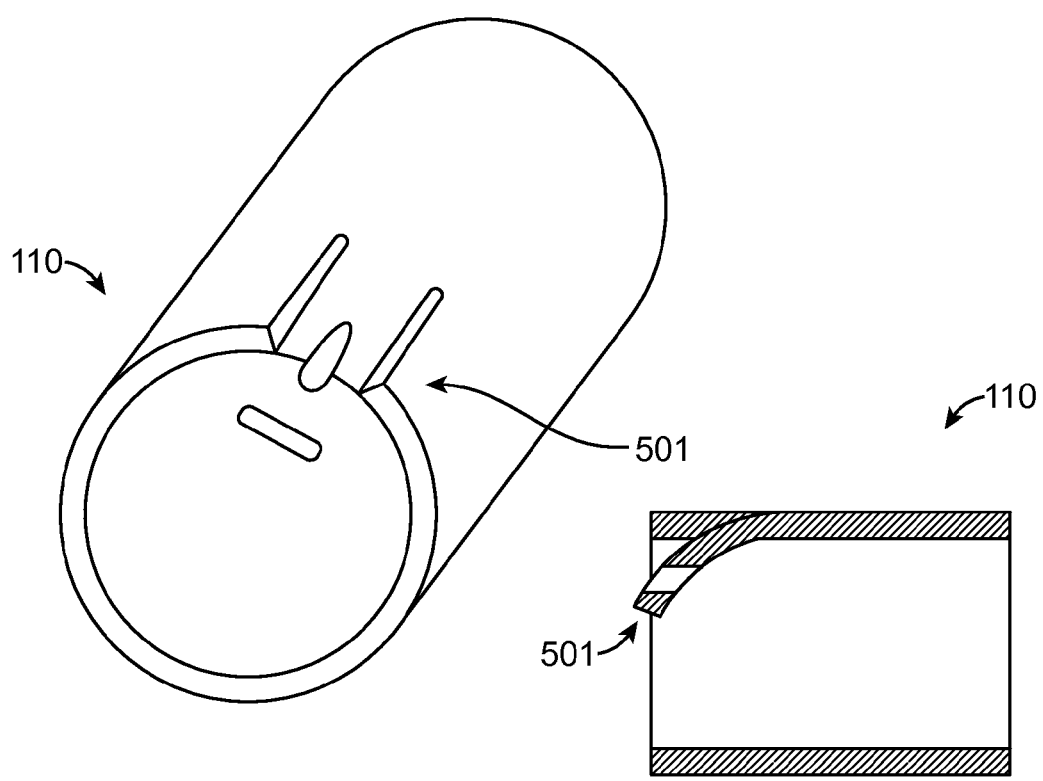
FIGS. 5A and 5B are perspective and side section views, respectively, of the coupling region which may utilize a superelastic/shape memory alloy affixed to proximal and/or distal member, according to many embodiments.

FIG. 1 provides a perspective of an example configuration of the convertible nephroureteral catheter 100. FIG. 2 details the coupling region of proximal member (catheter) 110 and distal member (stent) 120 with two example configurations shown. The release mechanism shown may comprise two elongated members—suture 130 and pull wire 140. As shown in FIG. 2, the suture 130 may exit through the wall of the proximal member 110 and reenter the distal member 120, holding the proximal and distal members 110, 120 together across the junction 150. The pull wire 140 can keep the suture 130 from pulling out until the pull wire (lock wire) 140 is removed or proximally retracted. The distal portion of the suture 130 may form a loop through which the distal portion of the pull wire 140 is threaded through. Additionally, an inner-member 160 may be included to cross the junction 150 on the inside to keep junction aligned (concentric) and facilitate passage of other components across the junction 150. Various configurations are shown in FIG. 2, where the suture 130 can be inside the inner member 160 and pass through the inner member 160 in addition to proximal and distal members 110, 120 (Configuration 2A). Alternatively or in combination, the suture 130 can be outside the inner member 160 and pass through only the proximal and distal members 110, 120 (Configuration 2B). Both the pull wire 140 and the suture 130 may be made of various suitable materials and shapes of materials, as well as other components. To release the locking suture 130, the pull wire 140 may be pulled proximally from a pull tab 170 on the handle portion or proximal hub 100a of the convertible catheter 100. FIGS. 3A and 3B detail an additional configuration of the suture loop 130 lock(s) which may wrap around inner member 160 as opposed to utilizing a pull wire 140 to achieve coupling. The distal portion of the suture 130 may form a loop through which the distal portion of the inner member 160 is threaded through (FIG. 3A). When the inner member 160 is retracted proximally, the distal loops of the suture 130 may be released which allows the proximal and distal members 110, 120 to separate. In some embodiments, the inner member 160, the proximal member 110, and the distal member 120 may form an interference fit with one another at the junction 150 to prevent displacement of the proximal and distal members 110, 120, although this interference fit may be decoupled by retraction of the inner member 160 relative to the junction 150. In some embodiments, the distal member 120 may comprise stops 125 along the inner surface of its lumen to restrict the distal advancement of the inner member 160 into the lumen (FIG. 3B).

FIGS. 4A-4D display enhanced perspectives of the coupling region between distal (stent) members 120 and proximal (catheter) members 110 of the device 100. Various elements which may be fabricated from metallic or polymeric materials, may be affixed to the coupling region of the proximal member 110. Shown by FIGS. 4A-4D is a large diameter tube segment 401 and joined to inner surface of said element 401 may be a small tube element 402. On the proximal member 120, a marker band 406 may be applied, with a ball wire 403 extending proximally from the marker band 406 and terminating at junction 150 (FIGS. 4A, 4B). The ball wire 403 may be passed through the small tube element 402 with the diameter of the ball wire 403 being slightly smaller than the inner diameter of the small tube element 402. Once the ball portion of ball wire 403 has fully passed through small tube element 402, a pull wire 405 can then be passed through small tube element 402 as in FIGS. 4C and 4D. The additive diameter of the pull wire 405 and the diameter of the ball wire 403, but not the ball itself, may not be greater than the inner diameter of the small tube element 402. The ball wire's 403 ball diameter plus the pull wire 405 diameter may exceed the inner diameter of the small tube 402, coupling the distal and proximal members 110, 120 until the pull wire 405 is removed. This pull wire 405 may be affixed to a region on the proximal hub 100a, allowing for removal by pulling it out of the device 100.

FIGS. 5A and 5B display proximal member 110 which may function in a similar fashion to the corresponding member 120 shown in FIGS. 4A-4D. The proximal member 110 may include a superelastic/shape memory element or tab 501 used to receive ball wire and pull wire components. This superelastic/shape memory element or tab 501 may function in a similar fashion to the small tube segment or element 402 shown in FIGS. 4A-4D. The tab 501 may replace the small tube segment or element 402 and the tab 501 may be integral to the proximal member 110. The tab 501 shown on the proximal member 110 may be heat set into a downward or upwards position to couple the distal member 120 and the superelastic properties of the tab 501 may enable it to relocate as an input is induced to the proximal hub 100a or interior lumen so as to allow a decoupling to occur. This tab

501, along with all other inner member components, may be situated anywhere along the entire length of the proximal member 110.

Figures 6A, 6B:
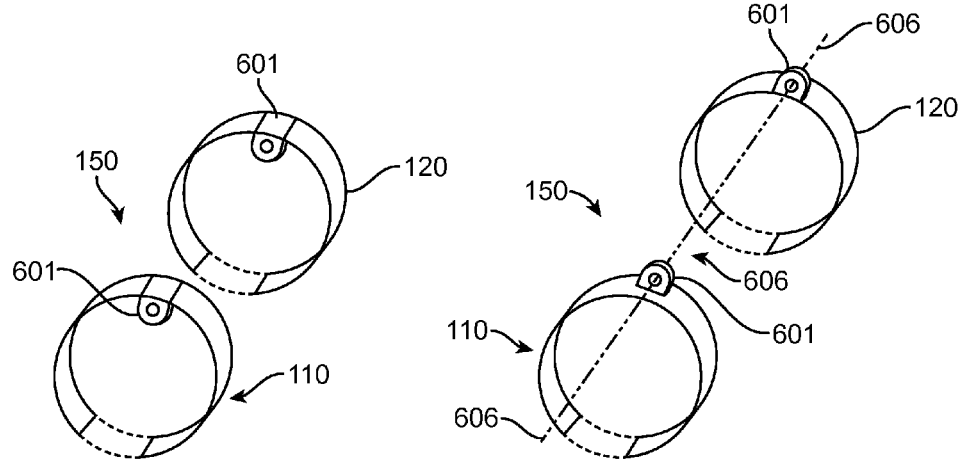
FIGS. 6A, 6B, and 6C are perspective views of a coupling region which utilizes locking ring elements to join proximal and distal members; and, FIG. 6D is a side section view of this coupling region.
Figures 6C, 6D:
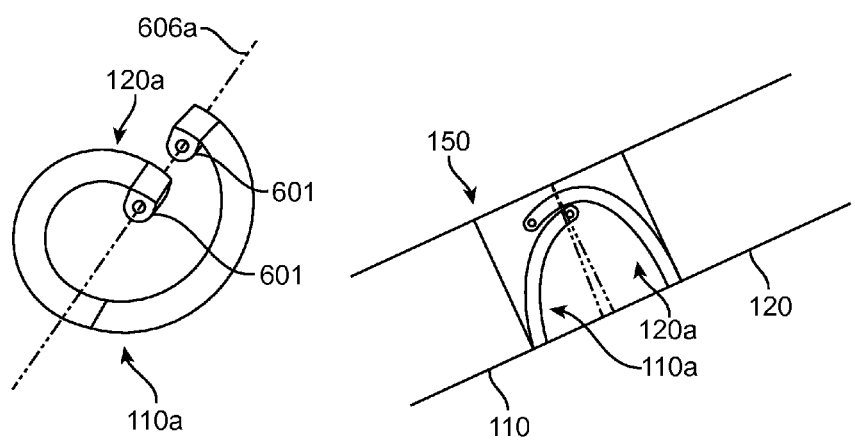

FIGS. 6A-6D show perspective views of the coupling region or junction 150 which utilizes locking ring elements 601 to join proximal and distal members 110, 120, which may be held coincident using a pull wire 606. FIG. 6A shows the proximal and distal members 110, 120 with locking ring elements 601 and FIG. 6B shows the same with the pull wire 606 threaded through the holes or apertures of the locking ring elements 601 to hold the proximal and distal members 110, 120 together. FIGS. 6C and 6D show locking ring elements 110a, 120b which may extend out from the interfacing ends of proximal and distal members 110, 120 at the junction 150. The two ring members 110a, 120a can be screwed (e.g., the ring members may have a high pitch such as a ¼ turn) and a wire 606a may lock the two ring members 110a, 120a in place. The two ring members 110a, 120a may be easily un-coupled once the wire 606a is removed. The locking ring elements 110a, 120a may have apertures or holes through which the pull wire 606a is threaded through.

Figure 7A:
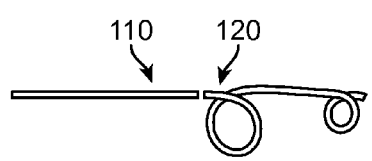
FIG. 7A is a side view of a coupling region which utilizes hexagonal elements affixed to proximal and distal members to achieve coupling.
Figure 7B:
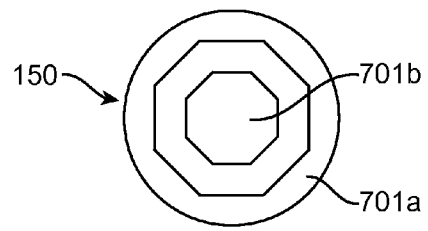
FIG. 7B shows a front section view of the coupling region.
Figure 7C:
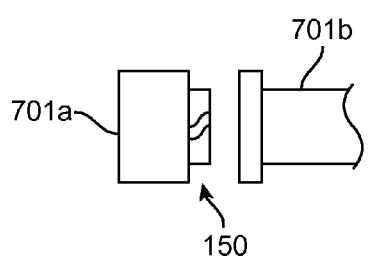
FIG. 7C shows a side view of the coupling region.
Figure 7D:
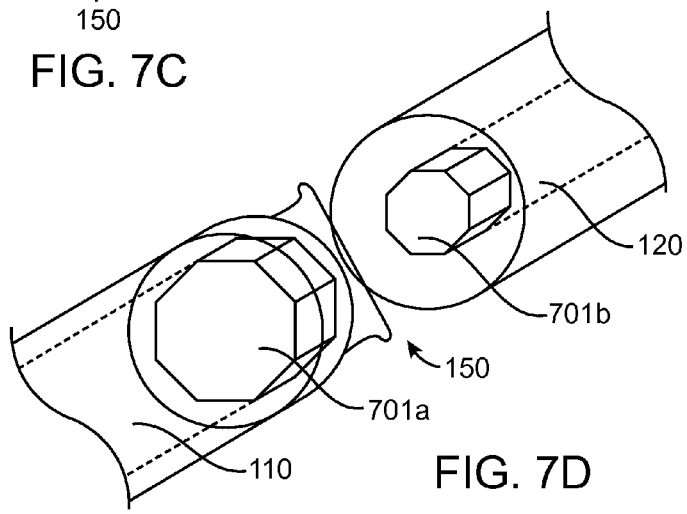
FIG. 7D shows a perspective view of the coupling region.
Figure 7E:
FIG. 7E shows a tool that may be used to actuate the hexagonal elements in the coupling region.
Figure 7F:
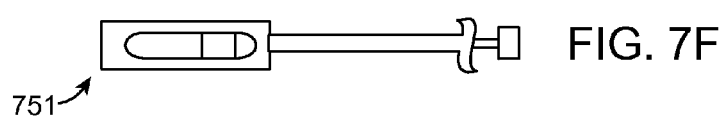
FIG. 7F shows a handle mechanism for the tool, according to many embodiments.

FIGS. 7A-7D show views of the coupling region or junction 150 which utilizes keyed (hexagonal shape shown to illustrate) elements affixed to proximal and distal members 110, 120 to achieve coupling. The inner member assembly coupling the stent to the catheter may be threaded/rotationally interlocked (like a ¼ turn or other thread) and keyed (e.g., hexed). As shown in FIG. 7A, one of the proximal or distal members 110, 120 may be held stationary while the other is turned to decouple the proximal and distal members 110, 120. A tool with coaxial members may be provided. The tool may hold one of the proximal or distal members 110, 120 stationary and can rotate the other to unscrew them. The tool may put down the catheter/proximal member 110 (i.e., advanced within the lumen of the catheter) to engage the inner member assembly at the time of disconnect. The stent/distal member 120 may be held steady and the part affixing the stent/distal member 120 to the catheter/proximal member 110 may be unscrewed. The catheter/proximal member 110 may be twisted while the stent/distal member 120 is decoupled. A pull wire may not be necessary with use of the tool to assist decoupling. FIG. 7B shows a side section view of the junction 150, showing a first keyed portion 701a coupled to the second keyed portion 701b. FIG. 7C shows a side view of the junction 150, showing the first keyed portion 701a in alignment with the second keyed portion 701b. FIG. 7D shows a perspective section view of the same. While hexagonal shapes for the keyed portions are shown, other shapes such as star or torx like shapes may be used instead. The present disclosure also provides a counter rotating tool 751 to engage and unlock proximal and distal portions 110, 120, without twisting the distal portion 120 (FIGS. 7E, 7F). The handle mechanism of the tool may allowed the keyed shape to be rotated while the outer bodies of the proximal and/or distal portions 110, 120 are held stationary.

Figure 8A:
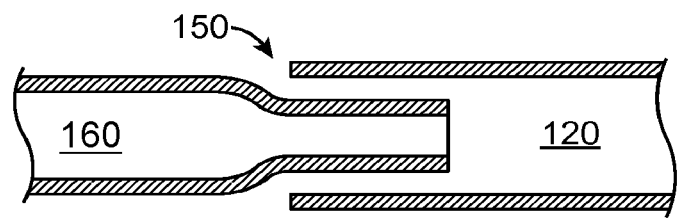
FIGS. 8A, 8B, and 8C shows side views of coupling configurations, according to many embodiments.
Figure 8B:
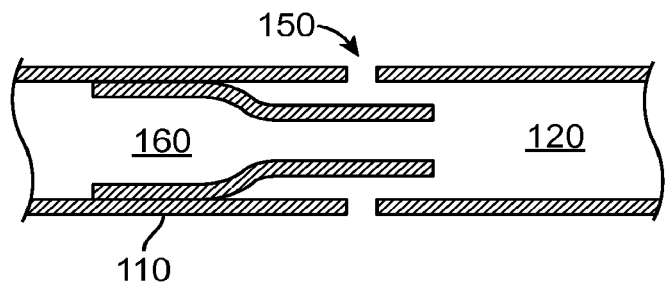
Figure 8C:
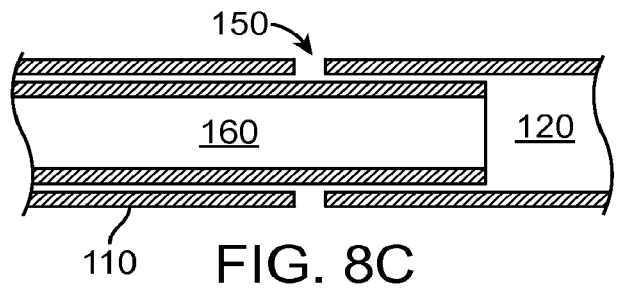

FIGS. 8A to 8B show side section views of the coupling region 150 in which the use of the inner member 160 of the catheter 100 is utilized in separate configurations to maintain concentricity between stent member 120 and catheter member 110. A variety of coupling mechanisms may be used with any of these inner member 160 configuration styles. FIG. 8A shows a configuration in which the functionality of the inner member 160 has been formed onto the distal tip of the catheter member 110. This distal tip of the catheter member 110 may slide into the lumen of the stent member 120. FIG. 8B shows a configuration whereby the inner member 160 does not extend back to the proximal hub 100a; this inner member 160 may be a component which is affixed to the catheter member 110 of the device 100 similar to the design style shown in FIGS. 4A-4D. FIG. 8C displays a configuration in which the inner member 160 extending fully back to the proximal hub 100a and being fixed into place at the hub region. The catheter distal tip may be formed to taper in toward the inside lumen of stent, it may utilize a fixed inner member at the catheter's distal end, or it may be a slidable component which may be fully removed from the catheter lumen.

Figure 9:
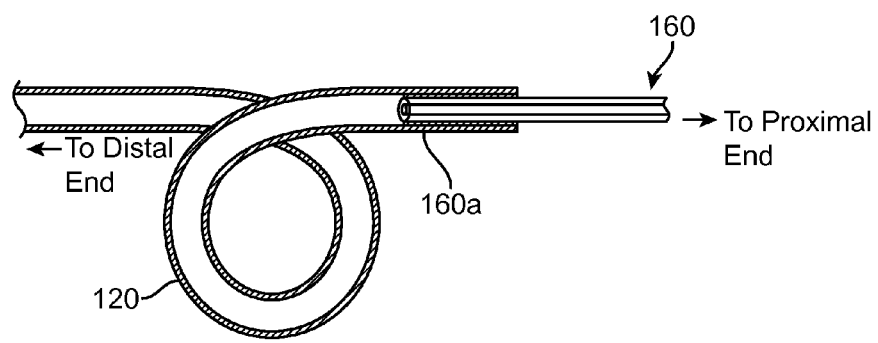
FIG. 9 shows a side section view of the application of an adhesive on inner member of catheter to achieve coupling between proximal and distal members, according to many embodiments.

FIG. 9 shows the use of an adhesive may be applied to the region of the inner member 160 region 160a which is in contact with the lumen of the stent member 110. This adhesive joint may effectively couple the inner member 160 and its corresponding outer catheter member 110 to the stent member 120 (outer catheter member 110 not shown in FIG. 9 or 10).

Figure 10:
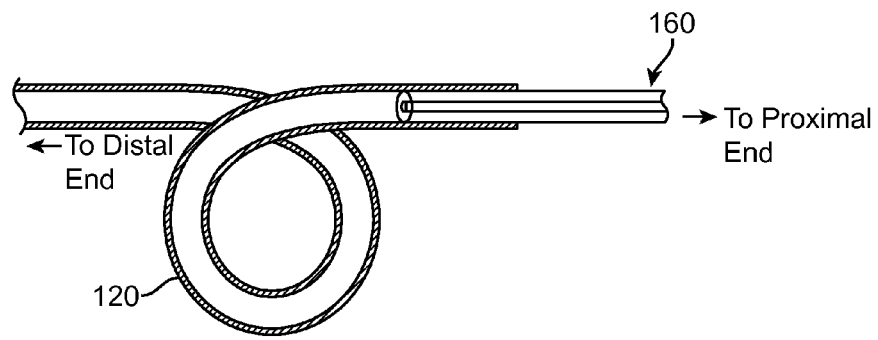
FIG. 10 shows a side section view of a friction/press fitting of the inner member of the catheter into the lumen of the stent to achieve coupling of proximal and distal members, according to many embodiments.

FIG. 10 shows the use of an interference fit where the inner member 160 has an oversized diameter, which when passed into the lumen of the stent member 120, a frictional fitting joint is achieved.

Figure 11A:
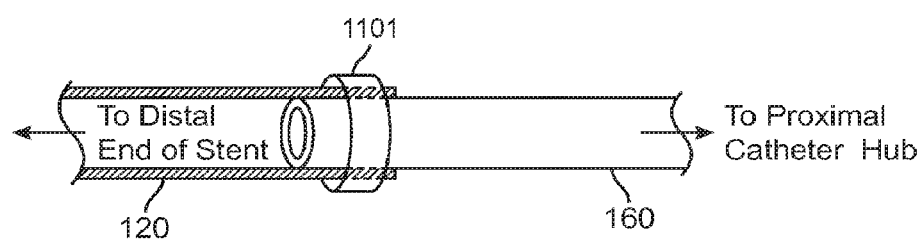
FIGS. 11A and 11B show side views of a metallic element applied to the outer surface of the stent to crimp a catheter inner member to achieve coupled state, according to many embodiments.
Figure 11B:
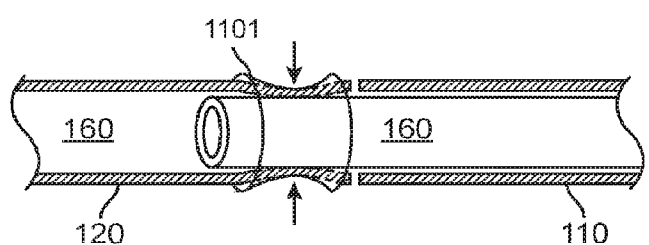

FIGS. 11A and 11B show the use of a metallic or polymeric crimp 1101 applied to the outside of the stent member 120, circumferentially collapsing that region over the inner member 160 of the catheter member 110 resulting in a coupled region.

Figure 12A:
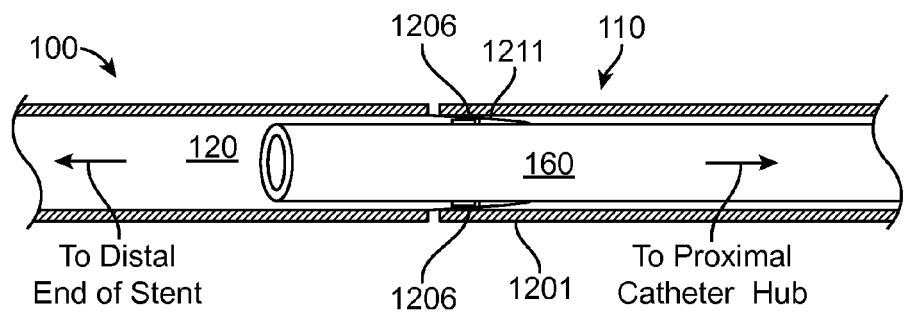
FIGS. 12A and 12B show side views of the use of a superelastic/shape memory alloy affixed to stent used to couple proximal and distal members, according to many embodiments.
Figure 12B:
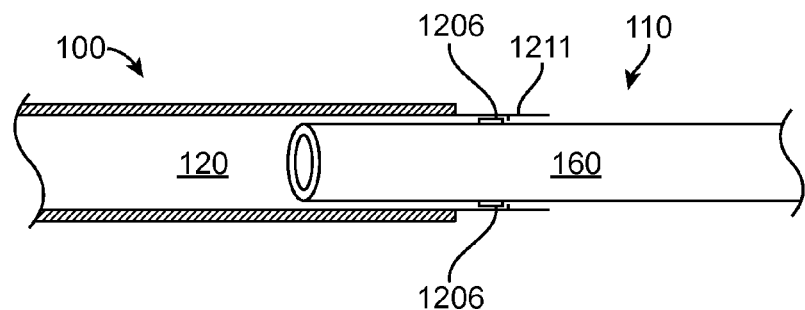

FIGS. 12A and 12B show the use of a superelastic/shape memory alloy which in this case has been affixed to the stent member 120 which may interface with protrusions 1206 affixed to the inner member 160 of the catheter 100. The stent member 120 may comprise a peel-away sheath 1201 acting as the catheter tube (FIG. 12A), whereby the peel away sheath 1201 would be the first element of the device 100 to be removed resulting in the release (shape alloy memory effect) of the wires grabbing protrusions 1206 on the outer surface of the inner member 160 from a super elastic component 1211 of the stent member 120, thus allowing for the complete removal of the inner member 160 thereafter.

Figure 13A:
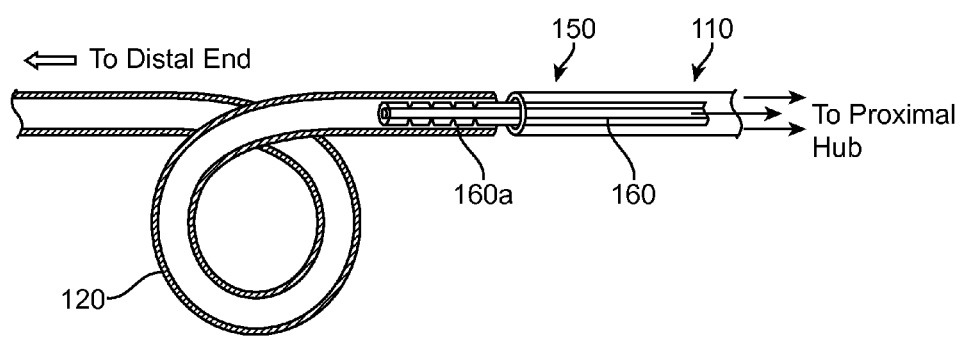
FIGS. 13A and 13B show side views of a method to couple proximal and distal members by thermally processing a region of stent, according to many embodiments.
Figure 13B:
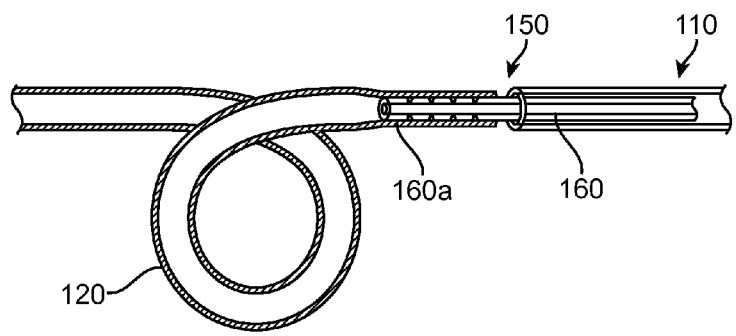

FIGS. 13A and 13B show where the region of the stent member 120 that interfaces with the inner member 160 is thermally processed. FIG. 13A shows the coupling region or junction 150 before processing and FIG. 13B shows the coupling region or junction 150 after processing. The inner member 160 may have a series of grooves 160a cut circumferentially about its surface, these grooves 160a serving as a region with which the polymer material of the stent member 120 may flow into when said region is heated. Once the stent member polymer is heated and has joined to the inner member 160, it is then allowed to cool permanently forming a mechanical interface between the two elements. A light to moderate pull force applied to the inner member 160 would allow it to break away from the stent member 120.

Figure 14:
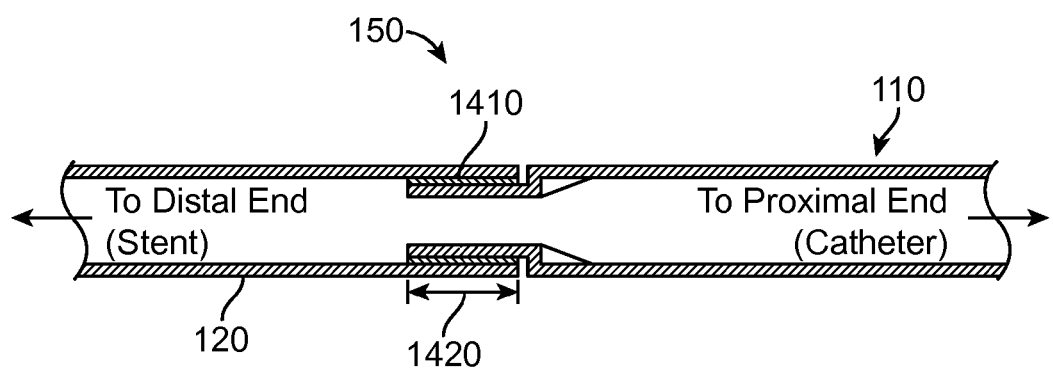
FIG. 14 shows a side section view detailing a threaded coupling whereby distal member (stent) has female threads (inner surface) and proximal member (catheter) has male threads over its outer surface within the coupling region, according to many embodiments.

FIG. 14 details a coupling configuration which permits the distal member (stent) 120 to receive a threaded proximal member (catheter) 110 into the lumen of the stent member 120. The female threaded coupling region 1420 of the stent member 120 may receive a proximal member 110 which has a male type thread arrangement 1410 over its outer surface within its coupling region 150. This permits proximal member 110 to be coupled to distal member 120 by threading into position and later proximal member 110 may be removed by unthreading (rotating) the proximal portion 110 of the device 100.

Figure 15A:
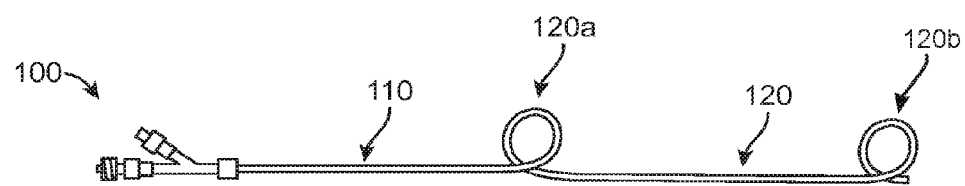
FIGS. 15A, 15B, and 15C show side views displaying the proximal loop suture and its independent functionality from the coupling mechanism, according to many embodiments.
Figure 15B:
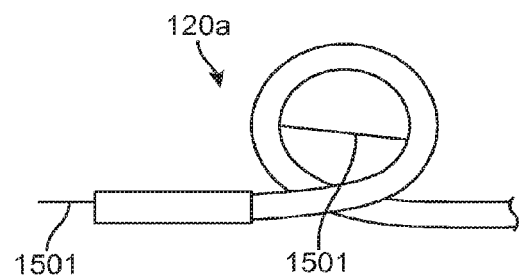
Figure 15C:
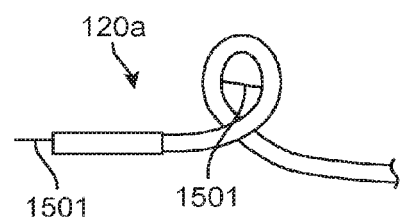

FIGS. 15A-15C depict the strand material used to close the proximal loop 120a of the distal portion (stent) 120 of the device 100 once it is within the renal pelvis of the kidney. This strand of material referred to as the proximal suture loop 1501 may pass through holes located through the sidewall of the bottom of the loop 120a. As the distal stent loop or curl 120b and the proximal stent loop or curl 120a are straightened for delivery, the distal curl 120b of the stent member 120 may reform upon straightener removal due to the large space in the bladder. The proximal loop 120a may need mechanical encouragement to reform in the tighter renal pelvis region. The present device 100 can use a proximal loop suture 1501 which is pulled in tension at the proximal hub 100a of the device 100 to reform the proximal loop 120a of the stent 120. This proximal loop suture 1501 may be removed by cutting one end of the strand at the hub 100a and pulling on the other end until it is fully removed. The proximal suture loop 120a and its function may act independently of the coupling mechanism.

Figure 16A:
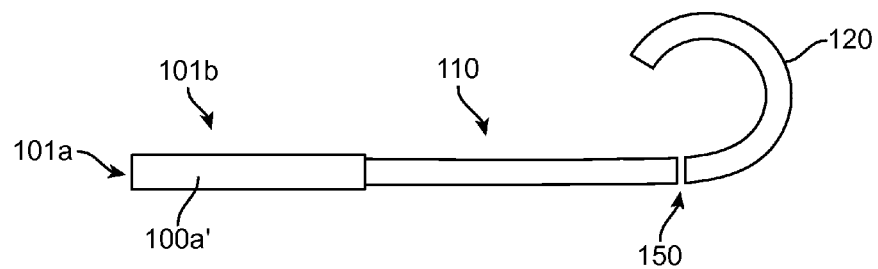
FIGS. 16A, 16B, and 16C show side views detailing several proximal hub configurations, according to many embodiments.
Figure 16B:
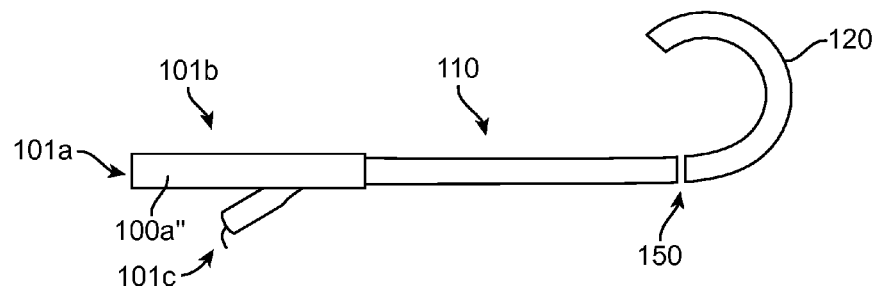
Figure 16C:
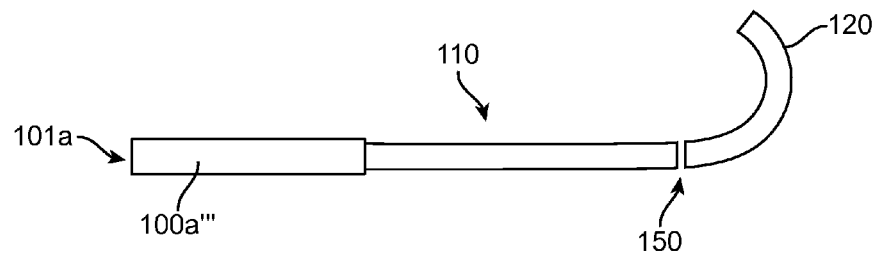

FIGS. 16A, 16B, and 16C display several configurations of proximal hubs. The coupling components may extend out from various hub configurations enabling removal and/or features such as a push button may permit decoupling of the device. That is, the pull wire(s) or suture loop(s) may be retracted from various ports of the proximal hubs. FIG. 16A shows a proximal hub 100a' with a main port 101a and a lateral port 101b. In an example, the suture loop 1501 may be proximally retracted from the lateral port 101b to facilitate the (re)formation of the proximal loop 120a and the pull wire 140 may be retracted from the main port 101a to release the stent member 120. FIG. 16B shows a proximal hub 100a" with a main port 101a and two lateral ports 101b, 101c. The additional lateral port 101c may, for example, be used for retraction of the suture 130 after the pull wire 140 has been retracted. FIG. 16C shows a proximal hub 100a'" with only a main port, which may be used for one or more of the pull wire(s) or suture(s). When the stent member 120 has been left implanted in the patient, the suture(s) may be one or more of cut, retracted, or left in place.

Further nephroureteral stent systems and joining or coupling mechanisms are described below. Many of the elements of the figures and their corresponding reference numbers are listed below.
  1: Stent
  2: Detachable drainage/delivery catheter
  3: Hub
  4: Loop suture lock
  5: Loop suture
  5a: Tensioning end of loop suture
  5b: Loop locking end of loop suture
  5c: Removal end w/tab (for lock suture proximal exit hole 20)
  6: Proximal loop
  7: Distal loop
  8: Distal radiopaque marker
  9: Proximal radiopaque marker
  10: Junction stent to drainage catheter (shown with gap for clarity)
  11: Lock Suture
  11a: Distal lock suture loop
  11b: Hub attachment (example of possible location)
  11c: Distal lock suture tie down
  12: Coupler, retractable
  13: Protective cap (pull wire)
  14: Protective cap (for loop suture 5)
  15: Lure thread connector (standard)
  16: Tapered tip
  16a: Drainage hole
  16b: Drainage hole
  17: Drainage holes (interior of loops)
  18: Lock/Release wire
  18a: Proximal part (going from coupler 12 to pull tab 19)
  18b: Distal end (going through lock distal lock suture loop 11a)
  19: Lock/Release wire pull tab
  20: Lock suture proximal exit hole
  21: Lock Suture Distal entry hole
  22: Distal reinforcement on stent (e.g., SS hypotube)
  23: Proximal reinforcement on catheter (e.g., SS hypotube)
  24: Alternative reinforcement or in combination with other reinforcement, higher durometer or tougher tubing than main body
  25: Advancement Stop
  26: Lock suture tie down reinforcement (swaged hypotube, for example, not shown swaged flush for clarity)
  27: Separate lock/release wire
  28: Inner member
  29: Fixed coupler
  30: Coupler to catheter attachment
  31: Slip fit
  32: Lock wire
  33: Wire As shown in FIGS. 17A-17F, a nephroureteral stent system 200 may comprise three major components: a distal and releasable stent or stent member 1, a catheter 2 and a hub 3, and a coupling and release mechanism which may comprise a loop suture 5, a lock suture 11, a retractable coupler 12, a lock/release wire 18, and a lock/release wire pull tab 19. The hub 3 may be fixed to the catheter 2, while the stent 1 may be releasably fixed to the catheter 2 at the junction 10 by the coupling and release mechanism. The coupling and release mechanism may operate in a manner similar to the coupling mechanisms described above and herein. For example, referring to FIG. 17C, the lock/release wire 18 may threaded through the distal lock suture hub attachment 11b of the lock suture 11, the lock/release wire may be retracted therefrom to release the lock suture 11 such that the stent 1 may decouple from the catheter 2, and the lock suture 11 may be proximally retracted further.

A straightener (e.g., a hypotube with a hub) can be put in to straighten the loops 6, 7 of the stent 1 out and the system 200 can be put over a guidewire in the body to be placed. The straightener can be then removed allowing the proximal and distal loops 6, 7 of the stent 1 to form. Usually, the proximal loop 6 will not form on its own in tight spaces and may need to be formed by pulling on the loop suture 5 similarly described above with reference to FIGS. 15a-15c.

As shown in FIGS. 17A-17F, one end of the loop suture 5c may be tied down to a pull tab 20, the loop suture going down the inner lumens of the catheter 2 and of the stent 1 to the proximal loop 6 where it may exit one drain hole 16a and re-enters another drain hole 16b and returns to the hub through the loop suture lock 4. The two drainage holes 16a, 16b may be configured so that when the loop suture 5 is tensioned, such as by pulling on tensioning end 5a, the loops suture 5 pulls the proximal loop 6 into a loop. The loop suture 5 can be locked in place by lock mechanism 4 to help retain the system 200 in the body. Additional drainage holes may exist on the proximal loop 6, generally residing on the inner portion of the loop 6.

In some embodiments, the nephroureteral systems may not need the loop suture 5 removed. In such systems, the loop suture lock 4 can be unlocked to free up the proximal loop 6 and the whole catheter 2 including the loop suture mechanism can be removed. Such systems may not require the distal lock suture tie down 5c and the lock suture proximal exit home 20; and instead, the ends of the loop suture 5 may be un-accessibly tied down in the hub 3. Nevertheless, it can be critical to be able to withdraw the loop suture 5 entirely before converting and releasing the stent 1. Hence, the distal lock suture tie down 5c and the lock suture proximal exit home 20 can be accessible.

The tension in the loop suture 5 can be relieved by unlocking the loop suture lock 4, which can allow the proximal loop 6 to relax and un-fold as the system 200 is removed through an access channel/hole.

Figure 18A:
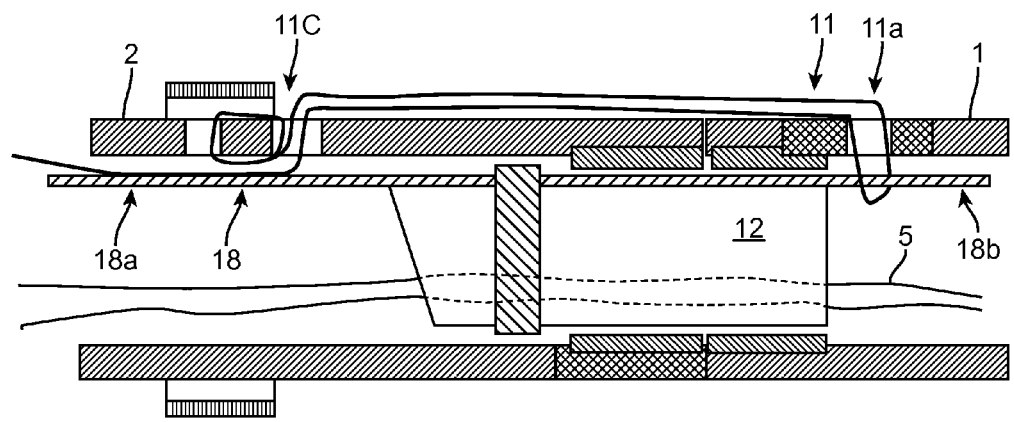
FIGS. 18A, 18B, and 18C show side section views of a coupling and release mechanism releasing the stent member of a nephroureteral stent system, according to many embodiments.
Figure 18B:
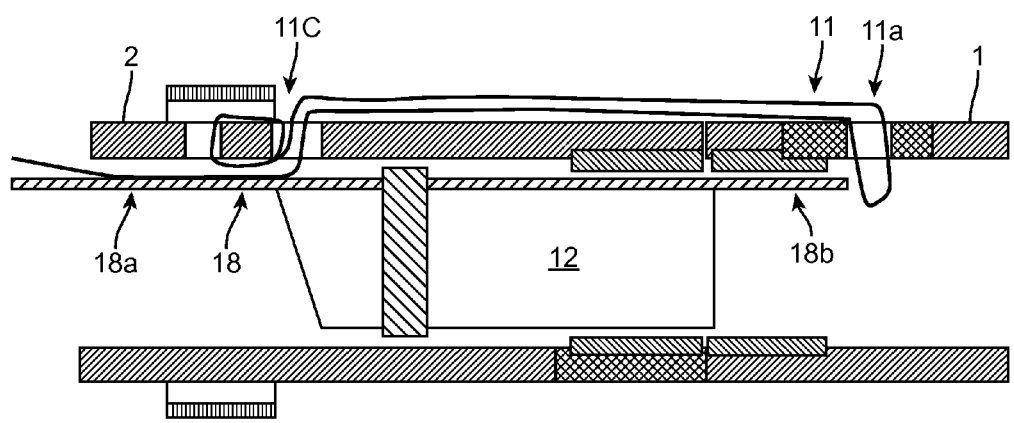
Figure 18C:
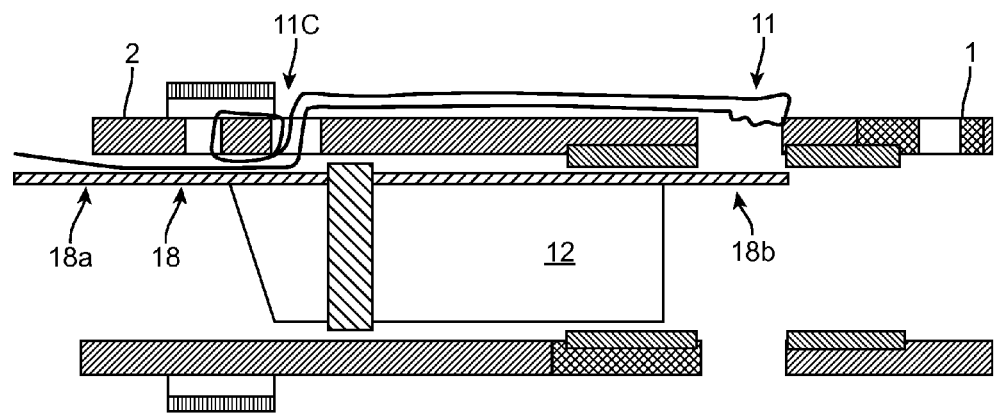

Referring to FIGS. 18A-18C, the coupling or lock mechanism for the system 200 can be similar to those described above and herein. The lock mechanism may comprise a lock wire (pull wire) 18 that may be permanently affixed to a coupler (e.g., a coupling cylinder) 12 of the inner member and may pass beyond the coupling cylinder 12 to engage or thread through the lock suture 11 at the distal lock suture tie down 11c as shown in FIG. 18A. As shown in FIG. 18B, the lock wire 18 may be retracted to free the distal lock suture tie down 11c. Such retraction frees the lock suture 11 and can retract the coupler 12 from the stent 1, allowing the lock suture 11 to be retracted and the stent 1 to be released.

Figure 19:
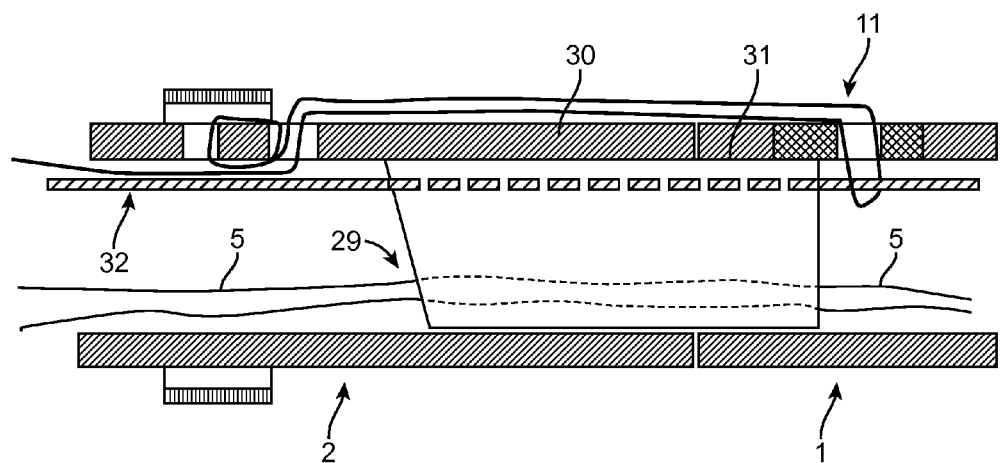
FIG. 19 shows a side section view of a side section view of a coupling and release mechanism for a nephroureteral stent system, according to many embodiments.
Figure 20:
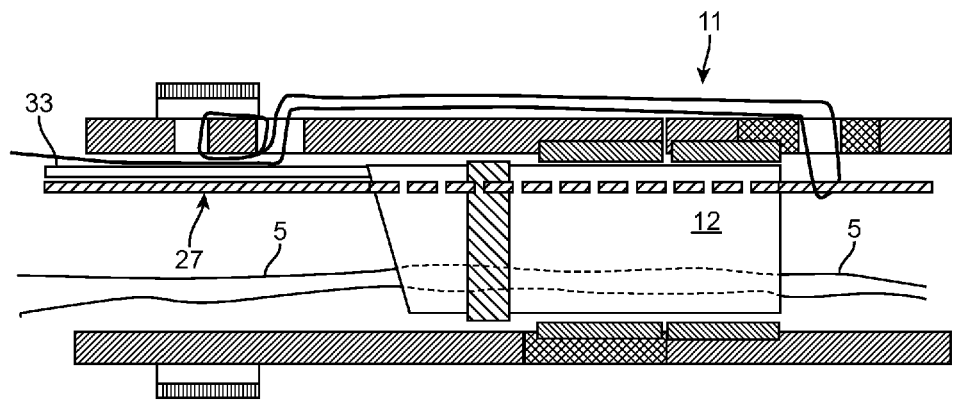
FIG. 20 shows a side section view of a side section view of a coupling and release mechanism for a nephroureteral stent system, according to many embodiments.
Figure 21:
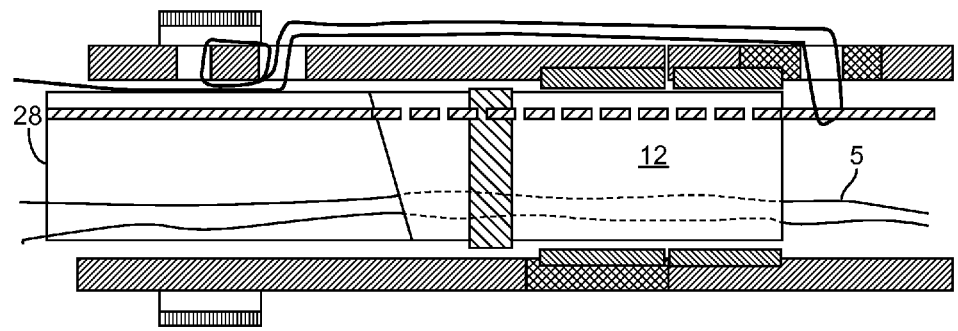
FIG. 21 shows a side section view of a side section view of a coupling and release mechanism for a nephroureteral stent system, according to many embodiments.

In some embodiments, a coupler cylinder 29 may be affixed to the catheter 2 through the coupler to catheter attachment 30 and may not be able to be independently pulled back (FIG. 19). A lock wire 32 retractable to free the lock suture 11 may be separate from the coupler 29. In some cases, however, the fixed coupler 29 may hang up on inside the stent 1 during removal (for example, due to friction, biofouling, etc.) if not pulled back independently.

In some embodiments, the coupler 12 may be connected to a wire 33 that is separate from the lock/release wire 27, and the wire 33 may be pulled as an additional step (which could be mitigated by interlocking the pullback actions).

In some embodiments, the coupler 12 may be attached to a co-axial inner member 28, which may be affixed to the hub so that it can be pull back. The coupler 12 may comprise an inner member, which may be solid polymer, nitinol, braided or coiled shafts (not shown).

Referring back to FIGS. 17A-17F, to deploy the stent portion 1, the operator may first unlock the loop suture 5, remove the loop suture cap 14, and pull the loop suture out. To actually deploy the stent 1, the cap 13 may be removed and the lock wire 18 may be pulled back by pulling the lock wire tab. The lock wire 18 may be in communication (e.g., attached) to the coupler 12 such that the coupler 12 may be pulled back while it is pulling out of the lock suture loop 11b, disconnecting the stent 1.

Figure 17A:
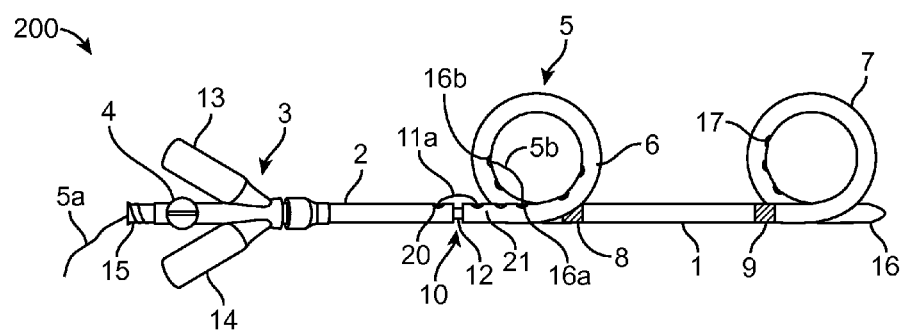
FIG. 17A shows a side view of a nephroureteral stent system, according to many embodiments.
Figure 17B:
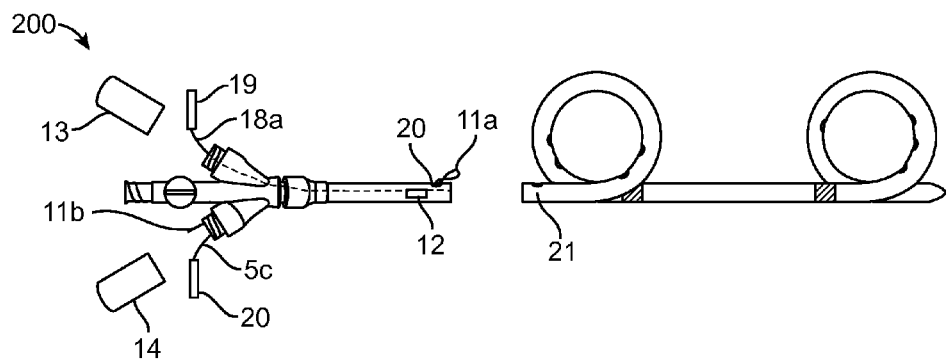
FIG. 17B show a side view of the nephroureteral stent system of FIG. 17A with the stent member detached.
Figure 17C:
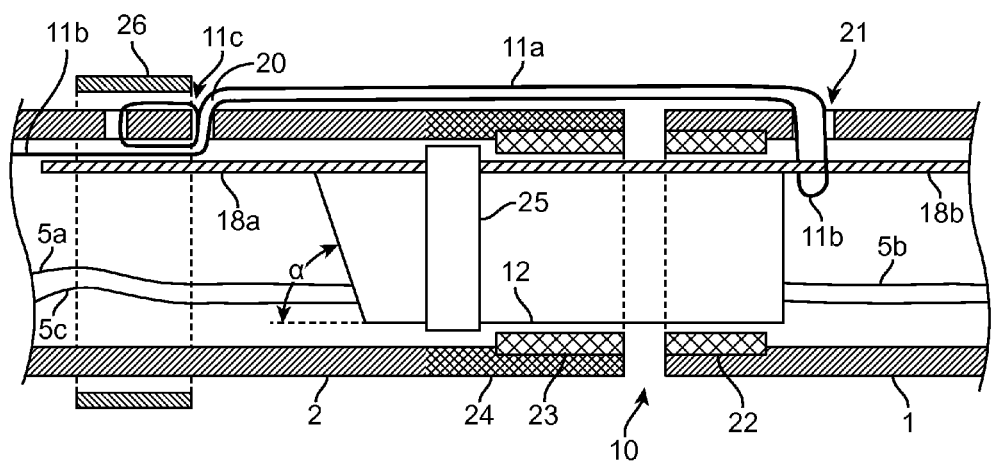
FIG. 17C shows a side section view of the coupling and release mechanism of the nephroureteral stent system of FIG. 17A.
Figure 17D:
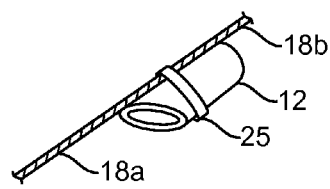
FIG. 17D shows a perspective view of the lock/release wire of the coupling and release mechanism of FIG. 17C.
Figure 17E:
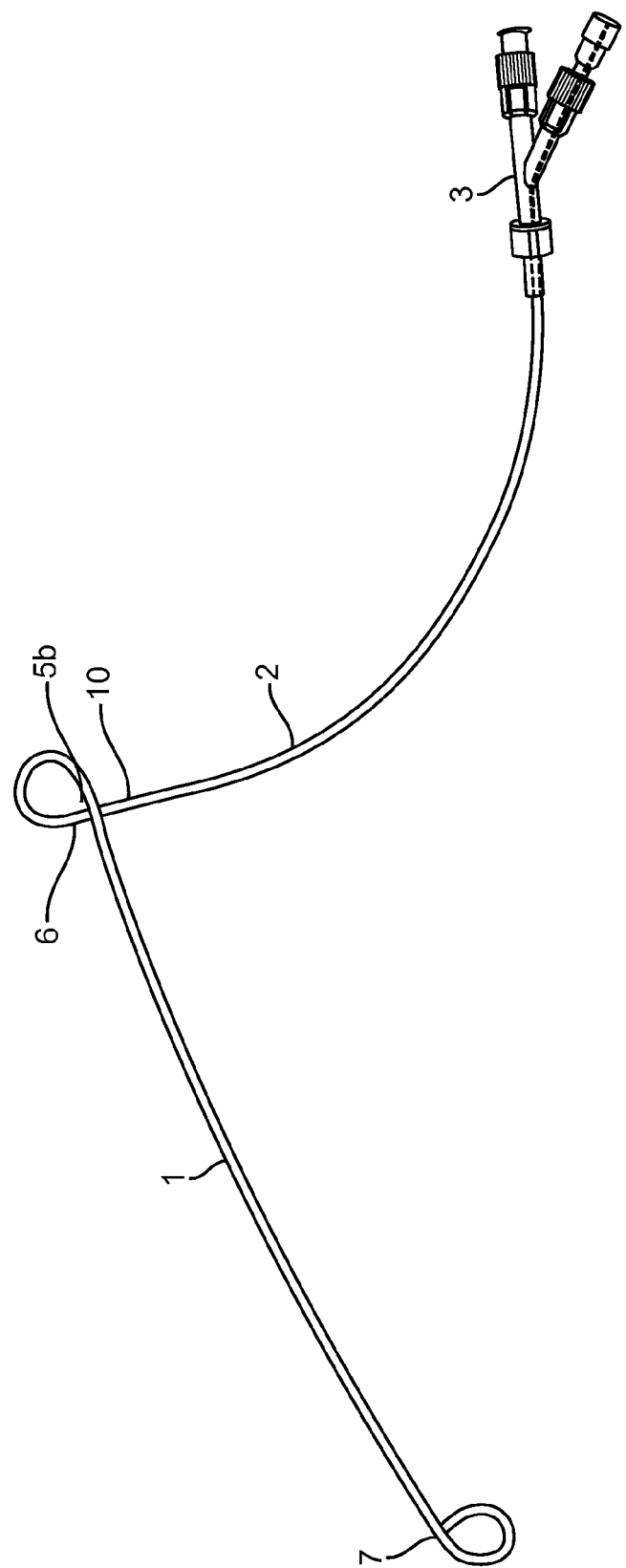
FIG. 17E shows a side view of the nephroureteral stent system of FIG. 17A.
Figure 17F:
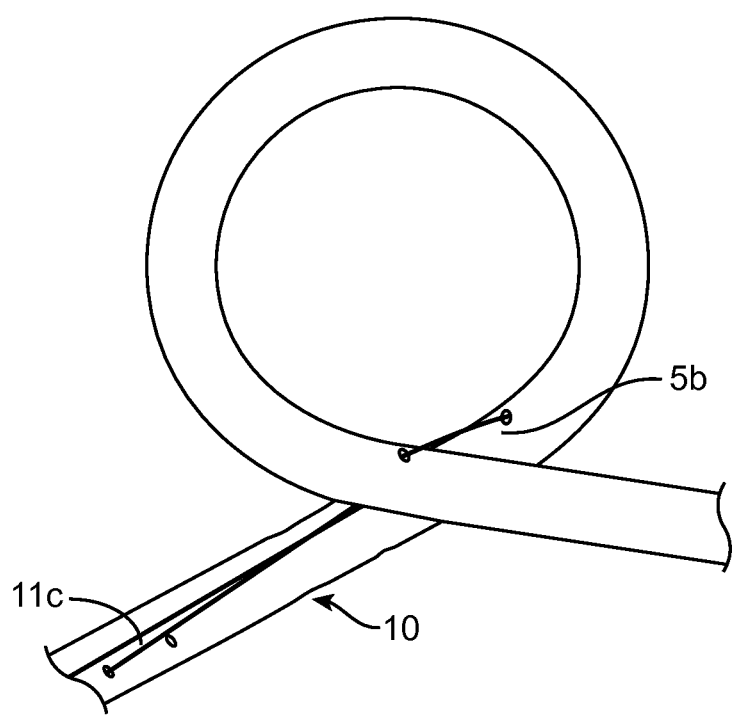
FIG. 17F shows a magnified view of the proximal loop of the stent member of the nephroureteral stent system of FIG. 17A.

As shown in FIG. 17C, an exemplary method of fixing the lock suture 11 is for one end 11c to be fixed near the distal end of the catheter 2 and the other end 11b fixed to the hub 3 for tensioning the catheter 2 and stent 1 together after the lock wire 18 is in place. Fixing one end 11c near the distal end of the catheter 2 while having the other end 11b be fixed more proximally can reduce instances of the catheter material pulling back or bunching up (and gaping at the junction) as the system 200 is advanced. Alternatively, both ends of the lock suture 11 can be tied down at the distal end or fixed down at the hub 3. The lock suture ends may be locked down or fixed by tying around two holes, gluing, embedding, swaging marker, etc.

The lock suture 11 may be made of a high tensile strength, low elongation material and flexible material like UHM-WPE (Spectra, Honeywell) or other material, including stainless steel or other metallic materials, or a combination of materials. It could be a single ribbon with a hole at the end to pass lock wire through, or other configurations.

The stiff coupler 12 may be made of implant grade materials such as stainless steel, NiTi, PEEK, or other materials know in the art. More flexible couplers are possible, but do not support the catheter 2 and stent 1 at the junction 10 under bending, resulting in splaying open of the junction 10.

Figure 22A:
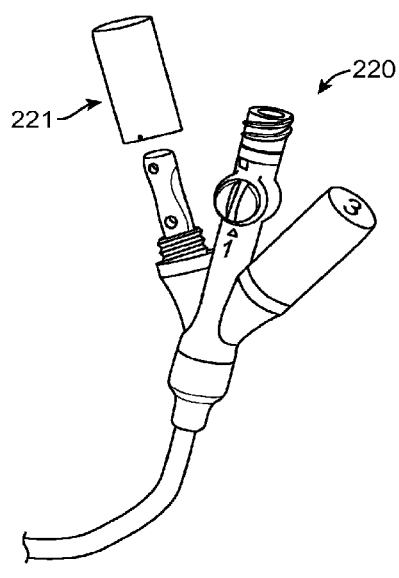
FIGS. 22A and 22B show perspective and perspective side section views of an exemplary hub for a nephroureteral stent system, according to many embodiments.
Figure 22B:
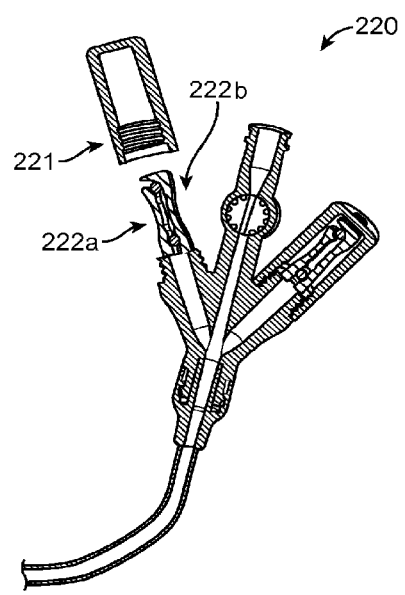
Figure 23A:
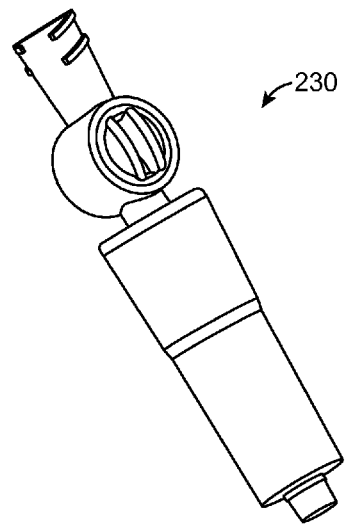
FIGS. 23A-23D show another exemplary hub for a nephroureteral stent system, according to many embodiments.
Figure 23B:
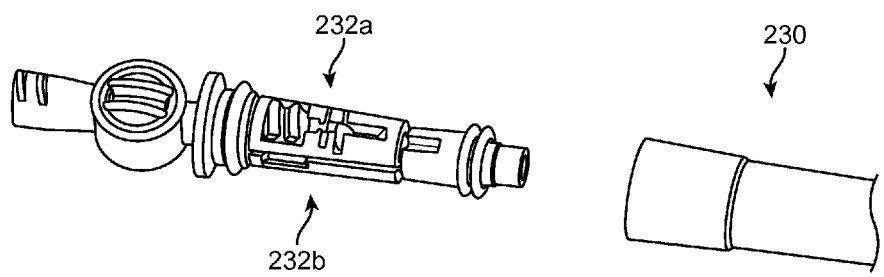
Figure 23C:
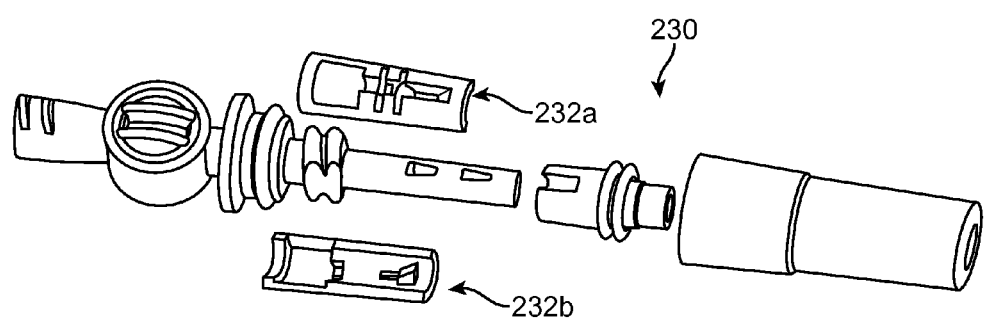
Figure 23D:
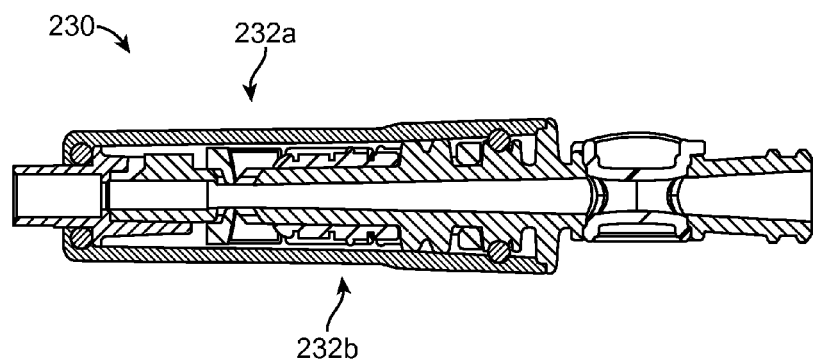
Figure 25A:
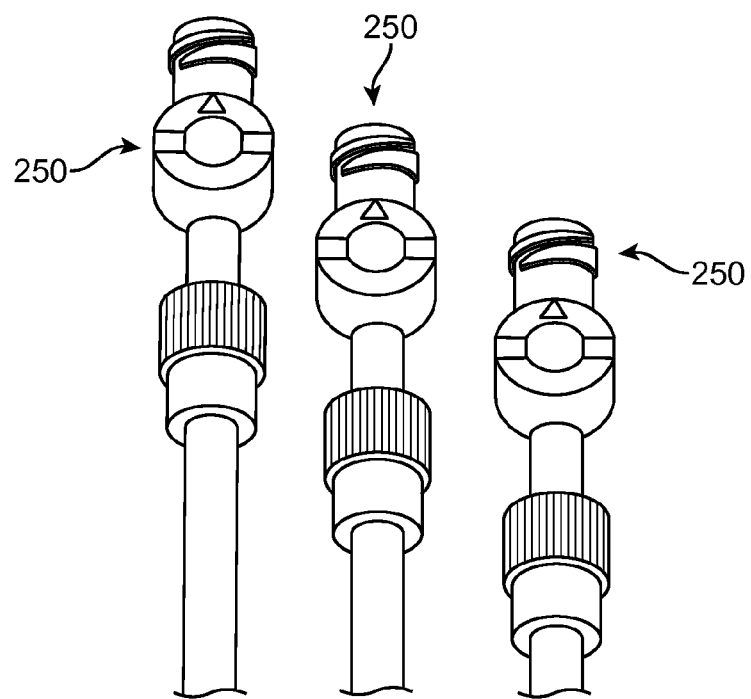
FIG. 25A show perspective views of various rotating hemostat type valves usable for various convertible stent systems, according to many embodiments.
Figure 25B:
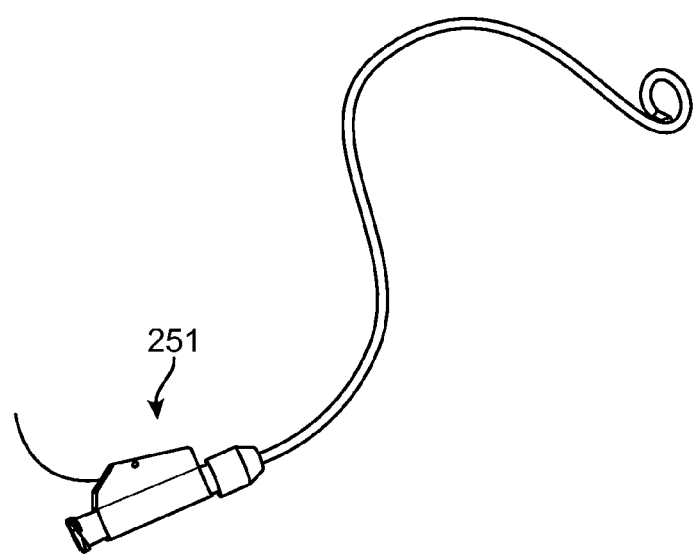
FIG. 25B shows a perspective view of a center lever lock usable for various convertible stent systems, according to many embodiments.

Various configurations of hubs are also disclosed, including a triple arm hub 220 which may be preferred in at least some cases (FIGS. 22A, 22B). A single side arm 221 of the triple arm hub 220 may comprise two pull tabs 222a, 22b. The hubs can be in axial configurations with pull tabs or laid out in a side arm or triple arm configuration. Alternatively, the hubs 220 could be axially stacked components (like rocket stages), that separate (unscrew for instance) in sequence to provide the necessary actions (FIGS. 23A, 23B, 23C). As shown in FIGS. 23B and 23C, the body of the hub 230 may be axially pulled apart so that pull tabs 232a, 232b may be accessed. A handle with a slide or twist mechanism may be used in some embodiments. The hubs shown may use a rotating hemostat type valve (shown in FIG. 25A by locks 250, for example) to wrap and lock the loop suture 5, although other mechanisms such as a center lever to lock the suture and seal out the side (shown in FIG. 25B, by lever mechanism 251, for example) may be used as well.

Figure 24:
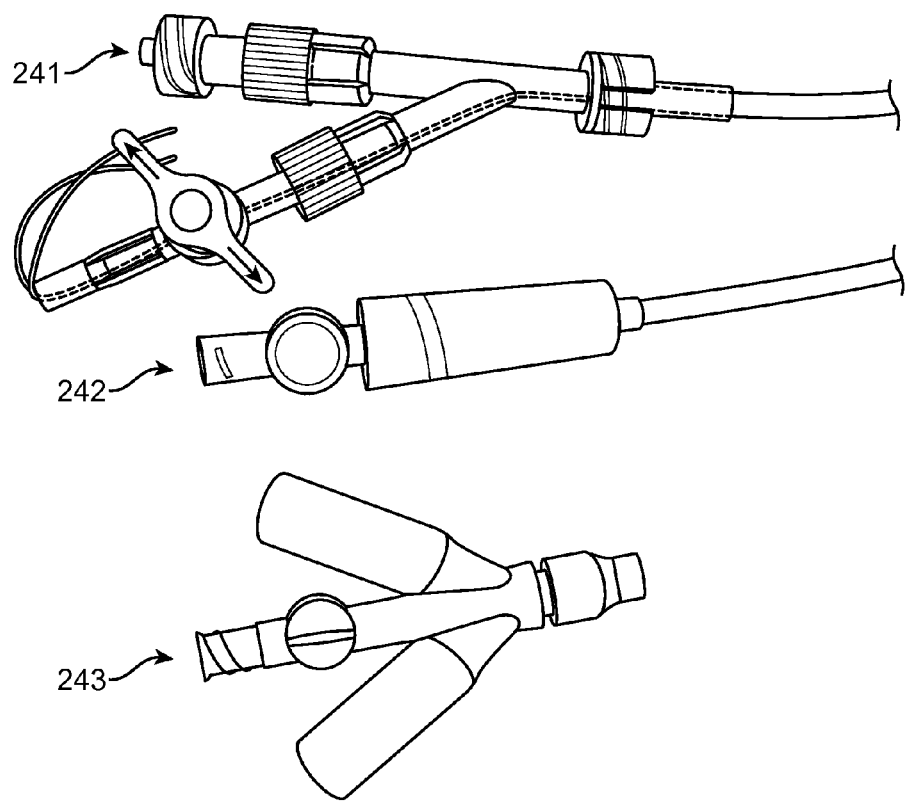
FIG. 24 shows further exemplary hubs for nephroureteral stent systems, according to many embodiments.

FIG. 24 shows further hubs that may be used for the devices 200, include a side armed hub 241, a barrel hub 242, and a triple armed hub 243.

In the side or triple arm hubs described above, the wire or sutures could be affixed directly to the caps, but may twist and bind if not provided a anti twist feature in cap. Since ports 15 on these devices 200 may need to be flushed periodically, a person un-familiar with the devices 200 might unscrew a cap inadvertently. Hence in preferred embodiments, pull tabs are separate from caps.

In some embodiments, the catheter 2 and the stent 1 may be decoupled from one another electrolytically or by electrical resistance based melting of a connector. The device 200 may comprise a sacrificial joint between the catheter 2 and the stent 1 that may dissolve in the presence of urine when an electrical charge is applied, similar to the mechanisms described in U.S. Pat. Nos. 5,122,136 and 5,643,254. The device 200 may use current resistance to soften or melt a connector, and since the connector may be internal to the catheter, no tissue may be affected by the temperature and the volume of body fluids flowing through the catheter may keep fluid temperatures within acceptable ranges. The device 200 may comprise shape memory component(s) and heating these components by electrical current can cause them change shape to release the catheter 2 and stent 1 from one another.

Figure 26:
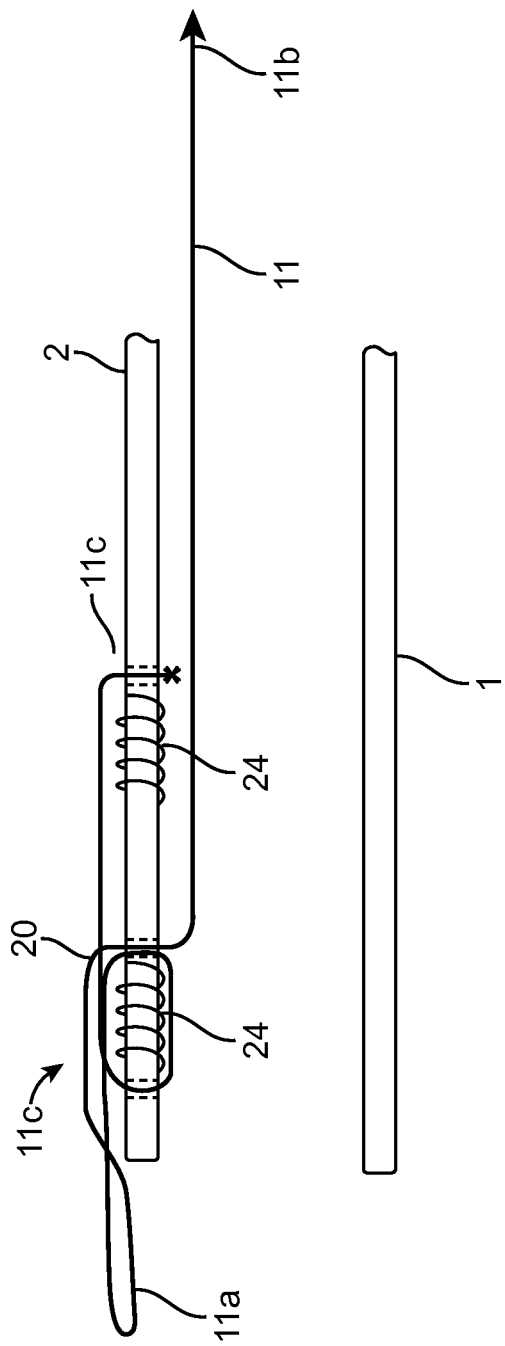
FIG. 26 shows a section view of a convertible stent system showing the arrangement of its loop suture, according to many embodiments.

As shown in FIG. 26, the lock suture 11 may be tied down to the catheter 2 at multiple distal lock suture tie down locations 11c. The catheter 2 may be reinforced at the tie down locations 11c with reinforcements 24. The reinforcements 24 may comprise coil reinforced areas. These coil reinforced areas may be provided so that the lock suture 11 does not tear through the material of the catheter 2 under high load scenarios, as discussed further below. In some embodiments, a coil or other mode of reinforcement would also be located in a region of the lock suture distal entry hole 21 of the stent 1.

Lock Suture Distal Termination Methods: At least one or both ends of the lock suture 11 may be terminated toward the distal end of the catheter 2 to prevent separation of the stent-catheter junction under loading scenarios during delivery of the device.

The suture 11 may be terminated on pull wire 19 by passing through the braid of the suture 11 itself or tie knot to pull wire shaft. The knot or braid may slide longitudinally over the wire 18 as it is displaced or removed during a detachment event.

The knotted suture 11 may terminate within the lumen of the catheter 2 which may leverage against a small diameter hole. The hole which suture knot leverages against may be covered with an adhesive, marker band, and/or other polymeric sheathing.

A hypotube or marker band may be applied or crimped to the outer diameter, inner diameter, or embedded within the surface of the catheter 2 and/or stent 1 polymer. The metallic surfaces of the applied hypotube or marker band may be utilized for attaching suture material.

Lock Suture Hole Reinforcement: The holes punched (e.g., punched using a coring tool) through the wall of the catheter 2 and stent 1 in which the lock suture 11 passes through may require reinforcement to enhance the tear resistance of the thermoplastic used in many device applications which may cause the catheter 2 and/or stent 1 to soften at body temperature for optimal patient comfort. Locking suture materials usable in some applications may have the propensity to tear through the holes in the wall of the device under high load scenarios. A stiff metallic, polymeric, or fibrous braid or coil may be embedded, extruded, or laminated within the wall of one or more of the stent 1 or the catheter 2 to prevent such tearing. A segment of hypotube or other high strength material may be embedded, overlaid, or affixed near the holes of interest, but typically only near that region so as to not greatly impact the overall comfort characteristics of the device, so the suture may leverage against this stiff substrate under load.

While the convertible catheter devices are described above as being used to deliver a nephroureteral stent, the convertible catheter devices and their methods of use may be applicable for other anatomical structures as well. The dimensions and/or material properties of the convertible catheter devices may be modified to be appropriate for the other anatomical structures. For example, convertible catheter devices according to many embodiments may be suitable for use as a biliary stent to maintain the patency of a bile duct; and, the convertible catheter device usable to deliver a biliary stent may have a smaller proximal loop or a J-hook configuration of the proximal hook suitable for the shape of the gallbladder and/or gallbladder neck. In another example, convertible catheter devices according to many embodiments may be suitable for use as an ileal conduit catheter. While the convertible catheter devices adapted for use as a nephroureteral stent may have a proximal to distal loop distance ranging from about 20 cm to about 28 cm, the convertible catheter devices adapted for use as ileal conduit catheters would have a longer loop to loop distance.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A stent delivery system comprising:
 a catheter body having an inner lumen and a proximal end and a distal end;
 a stent member having an inner lumen and a proximal end releasably coupled with the distal end of the catheter body;
 an inner member assembly disposed in the inner lumen of the catheter body and extending into the inner lumen of the stent member to concentrically align the catheter body and the stent member; and
 a tether extending through the inner lumen of the catheter body, then out through a lateral port of the catheter body near the distal end of the catheter body, then along outer surfaces of the catheter body and the stent member, and then through a lateral port of the stent member into the inner lumen of the stent member to form a loop over at least a portion of the inner member assembly, thereby securing the stent member to the catheter body,
 wherein the tether has a first end and a second end, the tether extending proximally toward both the first and second ends and the proximal end of the catheter body, and
 wherein retraction of the inner member from the inner lumen of the stent member frees the inner member assembly from the loop such that the stent member is released from the stent body.

2. The stent delivery system of claim 1, wherein the inner member assembly comprises a locking pull wire, the locking pull wire being threadable through the loop of the tether.

3. The stent delivery system of claim 1, wherein the inner member assembly comprises a hypotube.

4. The stent delivery system of claim 1, wherein the inner member assembly is configured to be actuated with one or more pull tabs or rotatable caps at a hub coupled to the proximal end of the catheter body.

5. The stent delivery system of claim 1, wherein the loop formed by the tether extends into the stent member through the lateral port of the stent member to be threaded through by the at least a portion of the inner member assembly within the inner lumen of the stent member.

6. The stent delivery system of claim 1, wherein the tether has a fixed end near the distal end of the catheter body and a free end, the tether extending proximally toward the free end and the proximal end of the catheter body.

7. The stent delivery system of claim 1, wherein the stent member comprises a proximal loop and a distal loop.

8. The stent delivery system of claim 7, wherein one or more of the proximal loop or the distal loop of the stent member have a straightened configuration and a looped configuration.

9. The stent delivery system of claim 8, wherein the one or more of the proximal loop or the distal loop is biased to assume the looped configuration.

10. The stent delivery system of claim 8, further comprising a loop pull wire extending through the inner lumen of the catheter body and coupled to the proximal loop, wherein retracting the loop pull wire pulls the proximal loop into the loop configuration or lowers a radius of the proximal loop.

11. The stent delivery system of claim 10, wherein the loop pull wire extends out from a first lateral port of the stent member near the proximal end of the stent member and extends back into a second lateral port of the stent member near a distal end of the proximal loop.

12. The stent delivery system of claim 10, wherein the loop pull wire is retractable from a pull tab or rotatable cap at a hub coupled to the proximal end of the catheter body.

* * * * *